(12) United States Patent
Kovach et al.

(10) Patent No.: US 8,541,458 B2
(45) Date of Patent: Sep. 24, 2013

(54) OXABICYCLOHEPTANES AND OXABICYCLOHEPTENES, THEIR PREPARATION AND USE

(75) Inventors: John S. Kovach, East Setauket, NY (US); Francis Johnson, Setauket, NY (US)

(73) Assignee: Lixte Biotechnology, Inc., East Setauket, NY (US)

( * ) Notice: Subject to any disclaimer, the term of this patent is extended or adjusted under 35 U.S.C. 154(b) by 0 days.

(21) Appl. No.: 13/493,816

(22) Filed: Jun. 11, 2012

(65) Prior Publication Data

US 2012/0264764 A1 Oct. 18, 2012

Related U.S. Application Data

(62) Division of application No. 12/460,404, filed on Jul. 17, 2009, now Pat. No. 8,227,473.

(60) Provisional application No. 61/137,691, filed on Aug. 1, 2008.

(51) Int. Cl.
*A61K 31/4178* (2006.01)

(52) U.S. Cl.
USPC ........................................ 514/389; 548/311.4

(58) Field of Classification Search
None
See application file for complete search history.

(56) References Cited

U.S. PATENT DOCUMENTS

| | | | |
|---|---|---|---|
| 2,957,906 A | 10/1960 | Erickson et al. | |
| 3,022,268 A | 2/1962 | Armitage et al. | |
| 3,954,913 A * | 5/1976 | Uebele et al. | 524/94 |
| 3,980,674 A | 9/1976 | Kubela et al. | |
| 4,143,054 A | 3/1979 | Sprague | |
| 4,218,478 A | 8/1980 | Omura et al. | |
| 4,298,752 A | 11/1981 | Dauben et al. | |
| 4,410,681 A | 10/1983 | Prindle | |
| 4,463,015 A | 7/1984 | Haslanger et al. | |
| 4,524,151 A | 6/1985 | Das et al. | |
| 4,614,825 A | 9/1986 | Snitman | |
| 4,654,355 A | 3/1987 | Nakane et al. | |
| 4,690,918 A | 9/1987 | Beppu et al. | |
| 4,816,579 A | 3/1989 | Thottathil et al. | |
| 4,851,423 A | 7/1989 | Girijavallabhan et al. | |
| 4,851,553 A | 7/1989 | Thottathil | |
| 5,047,574 A * | 9/1991 | Ohtani et al. | 560/120 |
| 5,266,710 A | 11/1993 | Patel et al. | |
| 5,326,898 A | 7/1994 | Chandraratna | |
| 5,763,647 A | 6/1998 | Ohtani et al. | |
| 5,770,382 A | 6/1998 | Hwang et al. | |
| 5,925,651 A | 7/1999 | Hutchinson | |
| 5,968,965 A | 10/1999 | Dinsmore et al. | |
| 6,222,055 B1 | 4/2001 | Wolter et al. | |
| 6,632,823 B1 | 10/2003 | Vernier et al. | |
| 6,696,483 B2 | 2/2004 | Singh | |
| 6,706,762 B1 | 3/2004 | Evans et al. | |
| 6,777,217 B1 | 8/2004 | Schreiber et al. | |
| 6,905,669 B2 | 6/2005 | DiMartino | |
| 6,949,624 B1 | 9/2005 | Liu et al. | |
| 7,067,551 B2 | 6/2006 | Remiszewski | |
| 7,154,002 B1 | 12/2006 | Bressi et al. | |
| 7,998,957 B2 | 8/2011 | Kovach et al. | |
| 8,058,268 B2 | 11/2011 | Kovach et al. | |
| 8,143,445 B2 | 3/2012 | Kovach et al. | |
| 8,227,473 B2 | 7/2012 | Kovach et al. | |
| 2002/0147345 A1 | 10/2002 | El Tayer et al. | |
| 2002/0177692 A1 | 11/2002 | Bartel | |
| 2003/0162186 A1 | 8/2003 | Bejanin et al. | |
| 2004/0010045 A1 | 1/2004 | Yi | |
| 2004/0053996 A1 | 3/2004 | Gesing et al. | |
| 2004/0087657 A1 | 5/2004 | Richon et al. | |
| 2004/0106141 A1 | 6/2004 | Mischel et al. | |
| 2004/0116366 A1 | 6/2004 | Monia et al. | |
| 2004/0122101 A1 | 6/2004 | Miller et al. | |
| 2004/0161475 A1 | 8/2004 | Ellison et al. | |
| 2004/0197888 A1 | 10/2004 | Armour et al. | |
| 2004/0209934 A1 | 10/2004 | McCluskey et al. | |
| 2004/0253637 A1 | 12/2004 | Buechler et al. | |
| 2005/0014839 A1 | 1/2005 | Kozikowski et al. | |
| 2005/0020831 A1 | 1/2005 | Inman et al. | |

(Continued)

FOREIGN PATENT DOCUMENTS

| | | |
|---|---|---|
| DE | 196 00 707 A1 | 7/1997 |
| EP | 1443967 | 1/2007 |

(Continued)

OTHER PUBLICATIONS

Eurasian Official Action issued May 24, 2012 in connection with Eurasian Patent Application No. 200970737 with English translation.
Non-final Office Action issued Sep. 20, 2012 in connection with U.S. Appl. No. 13/426,417.
Restriction Requirement issued Sep. 28, 2012 in connection with U.S. Appl. No. 13/492,816.
Fanghaemel, F. et al., Cycloaddition Reactions of (1,2)Dithiolo(1,2)dithiole Derivatives with Dimethyl Acetylenedicarboxylate: Formation of New Bi-, Tri- and Tetracyclic Thiopyran Derivatives, Synthesis, 10:1067-1071 (1994).
Honkanen et al. Regulators of Serine/Threonine Protein Phosphatases at the Dawn of a Clinical Era? Current Medicinal Chemistry 9, 2055-75 (2002).

(Continued)

*Primary Examiner* — Emily Bernhardt
(74) *Attorney, Agent, or Firm* — John P. White; Cooper & Dunham LLP

(57) ABSTRACT

This invention provides compounds having the structure

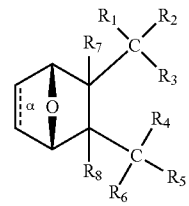

which may be used for the treatment of tumors.

9 Claims, 5 Drawing Sheets

(56) References Cited

U.S. PATENT DOCUMENTS

| | | |
|---|---|---|
| 2005/0054626 A1 | 3/2005 | Carter et al. |
| 2005/0119229 A1 | 6/2005 | Ammermann et al. |
| 2005/0136090 A1 | 6/2005 | Falotico et al. |
| 2005/0171202 A1 | 8/2005 | Graupner et al. |
| 2005/0203082 A1 | 9/2005 | Hsu et al. |
| 2005/0215526 A1 | 9/2005 | Hulme et al. |
| 2005/0222013 A1 | 10/2005 | Jung et al. |
| 2005/0272644 A1 | 12/2005 | Chung |
| 2005/0277583 A1 | 12/2005 | Yoshida et al. |
| 2005/0282893 A1 | 12/2005 | Au et al. |
| 2006/0030616 A1 | 2/2006 | McCluskey et al. |
| 2006/0117994 A1 | 6/2006 | Ryu et al. |
| 2006/0134682 A1 | 6/2006 | Roberts et al. |
| 2006/0167103 A1 | 7/2006 | Bacapoulos et al. |
| 2006/0235231 A1 | 10/2006 | Joel et al. |
| 2006/0264415 A1 | 11/2006 | Leit de Moradei et al. |
| 2007/0004771 A1 | 1/2007 | Lee et al. |
| 2007/0010669 A1 | 1/2007 | Breslow et al. |
| 2007/0049476 A1 | 3/2007 | Barlow et al. |
| 2007/0135365 A1 | 6/2007 | Tanizawa et al. |
| 2007/0135433 A1 | 6/2007 | Dean et al. |
| 2007/0155751 A1 | 7/2007 | Paruch et al. |
| 2007/0197550 A1 | 8/2007 | Georgopapadakou et al. |
| 2007/0208166 A1 | 9/2007 | Baly et al. |
| 2007/0213330 A1 | 9/2007 | Delorme et al. |
| 2008/0132503 A1 | 6/2008 | Moradei et al. |
| 2008/0214569 A1 | 9/2008 | Zhuang et al. |
| 2009/0012066 A1 | 1/2009 | Izumo et al. |
| 2009/0018142 A9 | 1/2009 | Zhuang et al. |
| 2009/0036309 A1 | 2/2009 | Kovach et al. |
| 2009/0055292 A1 | 2/2009 | Kovach et al. |
| 2009/0143445 A1 | 6/2009 | Kovach et al. |
| 2010/0029484 A1 | 2/2010 | Kovach et al. |
| 2010/0029640 A1 | 2/2010 | Kovach et al. |
| 2010/0029683 A1 | 2/2010 | Kovach et al. |
| 2011/0287537 A1 | 11/2011 | Kovach et al. |
| 2012/0135522 A1 | 5/2012 | Kovach et al. |

FOREIGN PATENT DOCUMENTS

| | | |
|---|---|---|
| JP | 50-69091 | 10/1973 |
| JP | 51-88631 | 1/1975 |
| JP | 10-504305 | 2/1996 |
| JP | 2002-520415 | 1/2000 |
| JP | 2001-329061 | 6/2000 |
| JP | 2004-531500 | 10/2002 |
| JP | 2006-519609 | 9/2004 |
| JP | 2005-507852 | 3/2005 |
| JP | 2007511528 | 5/2007 |
| JP | 2007514665 | 6/2007 |
| RU | 201598 C1 | 7/1994 |
| SU | 1553533 A1 | 3/1990 |
| WO | WO 91/18891 | 12/1991 |
| WO | WO 00/04023 | 1/2000 |
| WO | WO/00/04023 A1 | 1/2000 |
| WO | WO 02/09680 | 2/2002 |
| WO | WO/02/42310 A2 | 5/2002 |
| WO | WO/02/076989 A1 | 10/2002 |
| WO | WO/03/092616 A2 | 11/2003 |
| WO | WO 2004/080416 | 9/2004 |
| WO | WO 2005-018673 | 3/2005 |
| WO | WO 2005-049084 | 6/2005 |
| WO | WO 2005-058280 | 6/2005 |
| WO | WO 2005-074941 | 8/2005 |
| WO | WO 2006-023603 | 3/2006 |
| WO | WO 2006-129105 | 12/2006 |
| WO | WO 2007-014029 | 2/2007 |
| WO | WO 2007-021682 | 2/2007 |
| WO | WO 2007/092414 | 8/2007 |
| WO | WO/2007/092414 | 8/2007 |
| WO | WO 2007-118137 | 10/2007 |
| WO | WO/2008/028965 A2 | 3/2008 |
| WO | WO/2008/030617 A2 | 5/2008 |
| WO | WO 2008/058342 | 5/2008 |
| WO | WO/2008/097561 | 8/2008 |
| WO | WO/2009/020565 | 2/2009 |
| WO | WO/2009/045440 | 4/2009 |
| WO | WO/2010/014141 A1 | 2/2010 |
| WO | WO/2010/014220 | 2/2010 |
| WO | WO 2010/014254 | 2/2010 |
| WO | WO/2010/147612 | 12/2010 |

OTHER PUBLICATIONS

King, F.D. Bioisosteres, Conformational Restriction, and Pro-drugs—Case History: An Example of a Conformational Restriction Approach, Med. Chem. Principle & Practive, Chapter 14, p. 206-209 (1994).
Kwon et al. Depudecin induces morphological reversion of transformed fibroblasts via the inhibition of histone deacetylase, Proc. Natl. Acad. Sci. USA, 95(7), pp. 3356-3361 (1998).
Trost L. new Synthetic Reagents. Methithiomaleic Anhydride: A Synthon for Protected Carbomethoxyketne, J. Am. Chem. Soc. 99:7079 (1977).
Non-final Office Action issued Dec. 10, 2008 in connection with U.S. Appl. No. 11/703,401.
Non-final Office Action issued Mar. 30, 2009 in connection with U.S. Appl. No. 11/703,401.
Non-final Office Action issued Dec. 10, 2009 in connection with U.S. Appl. No. 11/703,401.
Final Office Action issued Aug. 17, 2010 in connection with U.S. Appl. No. 11/703,401.
Non-final Office Action issued Jun. 15, 2011 in connection with U.S. Appl. No. 11/703,401.
Non-final Office Action issued Mar. 12, 2012 in connection with U.S. Appl. No. 11/703,401.
Non-final Office Action issued May 26, 2011 in connection with U.S. Appl. No. 12/221,360.
Restriction Requirement issued May 18, 2011 in connection with U.S. Appl. No. 12/460,404.
Jun. 15, 2011 Response to May 18, 2011 Restriction Requirement issued in connection with U.S. Appl. No. 12/460,404.
Non-Final Office Action issued Aug. 3, 2011 in connection with U.S. Appl. No. 12/460,404.
Oct. 28, 2011 Response to Aug. 3, 2011 Non-final Office Action issued in connection with U.S. Appl. No. 12/460,404.
Final Office Action issued Dec. 15, 2011 in connection with U.S. Appl. No. 12/460,404.
Feb. 15, 2012 Amendment After Final in response to Dec. 15, 2011 Final Office Action issued in connection with U.S. Appl. No. 12/460,404.
Advisory Action issued Feb. 22, 2012 in connection with U.S. Appl. No. 12/460,404.
Mar. 9, 2012 Response to Feb. 22, 2012 Advisory Action issued in connection with U.S. Appl. No. 12/460,404.
Notice of Allowance issued Mar. 19, 2012 in connection with U.S. Appl. No. 12/460,404.
Non-final Office Action issued Sep. 30, 2010 in connection with U.S. Appl. No. 12/460,407.
Non-final Office Action issued Oct. 26, 2010 in connection with U.S. Appl. No. 12/069,147.
Non-final Office Action issued Jan. 4, 2011 in connection with U.S. Appl. No. 12/069,147.
Non-final Office Action issued Feb. 16, 2011 in connection with U.S. Appl. No. 12/221,360.
Non-final Office Action issued Feb. 16, 2011 in connection with U.S. Appl. No. 12/460,407.
Non-final Office Action issued Mar. 3, 2011 in connection with U.S. Appl. No. 12/482,182.
Non-final Office Action issued Mar. 18, 2011 in connection with U.S. Appl. No. 12/286,769.
International Search Report in connection with PCT/US2007/003095, issued Feb. 14, 2008.
International Preliminary Report on Patentability in connection with PCT/US2007/003095, issued Aug. 12, 2008.
Written Opinion in connection with PCT/US2007/003095, issued Feb. 14, 2008.
Notification of Transmittal of the International Search Report and the Written Opinion of the International Searching Authority, or the Declaration in connections with PCT/US07/03095, issued. Feb. 14, 2008.

Notification Concerning Transmittal of International Preliminary Report on Patentability in connection with PCT/US07/03095, issued Aug. 21, 2008.
Notification of Transmittal of the International Search Report and the Written Opinion of the International Searching Authority, or the Declaration in connection with PCT/US08/01549, issued May 16, 2008.
International Search Report in connection with PCT/US08/01549, issued May 16, 2008.
Written Opinion in connection with PCT/US08/01549, issued May 16, 2008.
Notification of Transmittal of the International Search Report and the Written Opinion of the International Searching Authority, or the Declaration in connection with PCT/US08/09330, issued Nov. 4, 2008.
International Search Report in connection with PCT/US08/09330, issued Nov. 4, 2008.
Written Opinion in connection with PCT/US08/09330, issued Nov. 4, 2008.
Notification of Transmittal of the International Search Report and the Written Opinion of the International Searching Authority, or the Declaration in connection with PCT/US08/11367, issued Dec. 12, 2008.
International Search Report in connection with PCT/US08/11367, issued Dec. 12, 2008.
Written Opinion in connection with PCT/US08/11367, issued Dec. 12, 2008.
Patent Search Report issued Oct. 25, 2011 in connection with Eurasian Patent Application No. 201170288, filed Jul. 30, 2009.
Supplemental European Search Report and European Search Opinion issued Apr. 2, 2012 in connection with European Patent Application No. 09803283.2, filed Jan. 24, 2011.
Notification of Transmittal of the International Search Report and the Written Opinion of the International Search Authority, or the Declaration, in connection with PCT/US09/04430, issued Jan. 12, 2010.
International Search Report in connection with PCT/US09/04430, issued Jan. 12, 2010.
Written Opinion in connection with PCT/US09/04430, issued Jan. 12, 2010.
Eurasian Official Action issued Nov. 19, 2009 in connection with Eurasian Patent Application No. 200970737.
Notification Concerning Transmittal of International Preliminary Report on Patentability in connection with PCT/US2008/001549, issued Aug. 11, 2009.
International Preliminary Report on Patentability in connection with PCT/US2008/001549, issued Aug. 11, 2009.
Supplemental European Search Report in connection with EP 08794986.3, issued Dec. 15, 2010.
International Preliminary Report on Patentability in connection with PCT/US2008/011367, issued Apr. 7, 2010.
Notification Concerning Availability of the Publication of the International Application in connection with PCT/US2008/011367, issued Apr. 9, 2009.
Notification of Transmittal of International Preliminary Report on Patentability in connection with PCT/US2008/011367, issued Apr. 15, 2010.
Notification of Transmittal of the International Preliminary report on patentability, in connection with PCT/US09/04108, issued Feb. 10, 2011.
Notification of Transmittal of the International Preliminary report on patentability, in connection with PCT/US09/04378, issued Feb. 10, 2011.
International Preliminary report on patentability, in connection with PCT/US09/04378, issued Feb. 1, 2011.
Notification of Transmittal of the International Preliminary report on patentability, in connection with PCT/US09/04430, issued Feb. 10, 2011.
International Preliminary Report on Patentability in connection with PCT/US09/04430, issued Feb. 1, 2011.
Supplemental European Search Report issued Mar. 9, 2011 in connection with European Patent Application No. 08725214.4, filed Sep. 2, 2009.

Communication pursuant to Rules 70(2) and 70a(2) EPC issued Mar. 28, 2011 in connection with European Patent Application No. 08725214.4, filed Sep. 2, 2009.
Eurasian Official Action issued Jun. 22, 2011 in connection with Eurasian Patent Application No. 200970737 with English translation.
International Search Report in connection with PCT/US09/04378, issued Sep. 18, 2009.
Written Opinion in connection with PCT/US09/04378, issued Sep. 18, 2009.
Notification of Transmittal of the International Search Report and the Written Opinion of the International Search Authority, or the Declaration, in connection with PCT/US09/04108, issued Sep. 15, 2009.
International Search Report in connection with PCT/US09/04108, issued Sep. 15, 2009.
Written Opinion in connection with PCT/US09/04108, issued Sep. 15, 2009.
Notification of Transmittal of the International Search Report and the Written Opinion of the International Search Authority, or the Declaration, in connection with PCT/US09/04378, issued Sep. 18, 2009.
Yur'ev et al. (1961), Chemical Abstracts, vol. 56, No. 73368.
Communication pursuant to Art. 94(3) EPC issued Jan. 30, 2013 in connection with European Patent Application No. 098032832, filed Jan. 24, 2011.
Japanese Office Action issued Jan. 22, 2013 in connection with Japanese Patent Application No. 2009-549092, including English language translation provided by Japanese Agent.
Registry (STN) Online, Nov. 16, 1984, Cas registered No. 57958-23-3 (Search Date Jan. 16, 2013).
Australian Office Action issued Dec. 6, 2012 in connection with Australian Patent Application No 2008214299.
Lu, S. Y. et al. "Aqueous ring-opening methathesis polymerization of 7-oxanorbornene derivates with oxygen-containing functionalities", Macromol. Chem. Phys., 1994, vol. 195, pp. 1273-1288.
CAS Registry No. 61531-23-5, Nov. 16, 1984 (discussed in the Australian Office Action cited as item 1 above).
Mexican Office Action issued Jan. 24, 2013 in connection with Mexican Patent Application No. MX/a/2009/008347, including English language summary provided by Mexican Agent.
Chinese Office Action issued Jan. 14, 2013 in connection with Chinese Patent Application No. 200880004292.9, including English language translation provided by Chinese Agent.
Mexican Office Action issued Jul. 19, 2012 in connection with Mexican Patent Application No. MX/a/2011/001007, including English language summary provided by Mexican Agent.
Mexican Office Action issued Sep. 25, 2012 in connection with Mexican Patent Application No. MX/a/2011/001007, including English language summary provided by Mexican Agent.
Baki, L. et al. (2004) "PS1 Activates PI3K thus inhibiting GSK-3 activity and tau overphosphorylation: effects of FAD mutations" the EMBO Journal 23:2586-259.
Baki, L. et al. (2008) "Wild-Type but not FAD mutant Presenilin-1 Prevents Neuronal Degeneration by Promoting Phosphatidylinositol 3-Kinase Neuroprotective Signaling" The Journal of Neuroscience 28:483-490.
Bummer, U.A. and Thiele, B.J. (2004) "The transiationally controlled tumor protein TCTP" International Journal at Biochemistry & Cell Biology 36:379-385.
Chen, S. et al. (2007) "Mcl-1 Down-regulation protentiates ABT 737 Lethality by Cooperatively Inducing Bak Activation and BAx Translocation" American Association for Cancer Research 6:782-791.
Chen, S.H. et al. (2007) "A kockout mouse approach reveals that TCTP functions as an essential factor for cell proliferation and survival in a tissue or cell type specific manner" Molecular Biology of the Cell 18:2525-2532.
Craig, R.W. (2002) "MCL1 provides a window on toe role of the BCL2 family in cell proliferation, differentiations and tumorigenesis" Leukemia 16:444-454.
Engel, T. et al. (2006), The journal of Neurosciences 26:5083-5090.
Fabel et al. (2001) "Long term stabilization in patients with malignant glioma after treatment with liposomal doxorubicin" Caner, vol. 92, No. 7, pp. 1936-1942.

Levesque, (2004) Reduction of L-DOPA-induced dyskinesias by retinoid agonists: a new way to improve Parkinson's disease treatment. The Parkinson Alliance, 2004 Pilot Study Grants (Abstract Only).

Marks at al. (2003), Histone Deacetylases, Curr. Op. Pharm. 3:344-351.

Tuynder, M. et al. (2004) "Translationally controlled tumor protein is a target of tumor reversion" PNAS 101:15364-15369.

Yoshida et al. (1999) "Trichostacin and Leptomycin Inhibition of Histone Deacetylation and Signal-Dependent Nuclear Export" Ann N.Y. Acad. Sci., 886, pp. 23-35.

Eurasian Official Action issued Nov. 19, 2012 in connection with Eurasian Patent Application No. 201170288, filed Jul. 30, 2009, including English language translation provided by Eurasian Agent.

Communication pursuant to Art, 94(3)EPC issued Dec. 12, 2012 in connection with European Patent Application No. 08725214.4, filed Sep. 2, 2009.

Notice of Allowance isued Dec. 28, 2012 in connection with U.S. Appl. No. 13/174,249.

Abel et al. (2008), "Epigenetic targets of HDAC inhibition in neurodegenerative and psychiatric disorders", Curr. Opin. Pharmacol., 8, pp. 57-64.

Acharya et al. (2005), "Rational development of histone deacetylase inhibitors as anticancer agents: a review", Mol. Pharmacol., 68, pp. 917-932.

Adcock, I. (2007), "HDAC Inhibitors as anti-inflammatory agents" Br. J. Pharm., vol. 150, pp. 829-831.

Albert, M. S. (2007), "Changing the Trajectory of Cognitive Decline?" N. Engl. J. Med., 357(5), pp. 502-503.

Andrabi, S. et al. (2007), "B. Protein Phosphatase 2A regulates life and death decisions via Akt in a context-dependent manner," Proc. Natl. Acad. Sci USA 104:19011-19016.

Avila et al. (2006), "Tau phosphorylation, aggregation, and cell toxicity" J. Biomedicine and Biotechnology, Hinwadi Publishing Corporation, vol. 2006, pp. 1-5.

Ayaydin, F. et al. (2000), "Inhibition of serine/threonine specific protein phosphatases causes premature activation of cdc2MsF kinase at G2/M transition and early mitotic microtubule organization in alfalfa." The Plant Journal, 23:85-96.

Baskin, T. and Wilson, J. (1997), "Inhibitors of protein kinases and phosphatases alter root morphology and disorganize cortical microtubules." Plant Physiol. 113:493-502.

Bastien et al. (2004), "Nuclear retinoid receptors and the transcription of retinoid-target genes." Gene, vol. 328, pp. 1-16.

Berthold, F., et al. (2005), "Myeloablative megatherapy with autologous stem-cell rescue versus oral maintenance chemotherapy as consolidation treatment in patients with high-risk neuroblastoma: a randomised controlled trial." Lancet Oncol., 6:649-658.

Bertini et al. (2009), "Structural basis of serine/threonine phosphatase inhibition by the archetypal small molecules cantharidin and norcantharidin," J. Med. Chem. 52, 4838-43.

Beglopoulis et al. (2006), "Regulation of CRE-dependent transcription by presenilins: prospects for therapy of Alzheimer's disease" Trends Pharmacol. Sci., 27(1), pp. 33-40.

Blaheta, A. et al. (2002), "Valproate and Valproate-Analogues: potent Tools to Fight Against Cancer," Current Medicinal Chemistry, vol. 9 pp. 1417-1344.

Blaskovich et al. (2002), "Recent discovery and development of protein tyrosine phosphatase inhibitors." Expert Opinion on Therapeutic Patents. vol. 12, No. 6, pp. 871-905.

Burke, R. E. (2007), "Inhibition of mitogen-activated protein kinase and stimulation of Akt kinase signaling pathways: Two approaches with therapeutic potential in the treatment of neurodegenerative disease" Pharmacology and Therapeutics, 114, pp. 261-277.

Camphausen et al. (2005), "Influence of in vivo growth on human glioma cell line gene expression: Convergent profiles under orthotopic conditions." Proc. Natl. Acad. Sci. USA, vol. 102, No. 23, pp. 8287-8292.

Chang, Q., et al. (2007), "All-trans-retinoic acid induces cell growth arrest in a human medulloblastoma cell line" J. Neurooncol, 84:263-267.

David et al. (1998), "Histone deacetylase associated with mSin3A mediates repression by the acute promyelocytic leukemia-associated PLZF protein" Oncogene, 16, 2549-2556.

Drewinko et al. (1967), "Combination chemotherapy in vitro with adriamycin. Observations of additive, antagonistic, and synergistic effects when used in two-drug combinations on cultured human lymphoma cells," Cancer Biochem. Biophys., vol. 1, pp. 187-195.

Erdodi et al. (1995), "Endothall thioanhydride inhibits protein phosphatases-1 and -2A inhibition, and anticancer activity," Am. J. Physiol. (Cell Physiol.) vol. 38, pp. C1176-C1184.

Essers, M. et al., (2001), "Synthesis of the first fluorinated cantharidin analogues." Tetrahedron Lett., 42, 5429-5433.

Finnin et al. (1999), "Structures of a histone deacetylase homologue bound to the TSA and SAHA inhibitors" Nature, 401, pp. 188-193.

Fischer et al. (2007), "Recovery of learning and memory is associated with chromatin remodeling" Nature, vol. 447, pp. 178-183.

Flicker et al. (1997), "Tyrosine kinase signaling pathways control the expression of retinoic acid receptor-a in SK-BR-3 breast cancer cells." Cancer Lett., vol. 115, pp. 63-72.

Furumai et al. (2001), "Potent histone deacetylase inhibitors built from trichostatin A and cyclic tetrapeptide antibiotics including trapoxin" Proc. Natl. Acad. Sci. USA, 98(1), pp. 87-92.

Giannini, R. and Cavallini, A. (2005), "Expression analysis of a subset of coregulators and three nuclear receptors in colorectal carcinoma." Anticancer Research, vol. 36, No. 6B, pp. 4287-4292.

Gottlicher, M et al. (2001), "Valproic acid defines a novel class of HDAC inhibitors inducing differentiation of transformed cells," EMBO Journal, vol. 20, No. 24, pp. 6969-6978.

Gumireddy, K., et al. (2003), "All-trans-Retinoic Acid-induced Apoptosis in Human Medulloblastoma: Activation of Caspase-3/Poly(ADPribose) Polymerase 1 Pathway." Clinical Cancer Research, 9:4052-4059.

Hart, ME et al. (2004), "Modified norcantharidine: synthesis, protein phosphatases 1 and 2A inhibition, and anticancer activity," Bioorganic & Medicinal Chemistry Letters, vol. 14, pp. 1969-1973.

Havrilesky, LJ et al. (2001), "Relationship between expression of coactivators and corepressors of hormone receptors and resistance of ovarian cancers to growth regulation by steroid hormones," J. Soc. Gynecol. Investig., vol. 8, pp. 104-113.

Hermanson et al. (2002), "N-CoR controls differentiation of neural stem cells into astrocytes," Nature, vol. 419 pp. 934-939.

Hildmann et al. (2007), "Histone deacetylases-an important class of cellular regulators with a variety of functions", Appl. Microbiol. Biotechnol., vol. 75, pp. 487-497.

Hill et al. (2007), "Heterocyclic substituted cantharidin and norcantharidin analogues—synthesis, protein phosphatase (1 and 2A) inhibition, and anti-cancer activity" Bioorg. Med. Chem, Lett., 17, pp. 3392-3397.

Hong et al. (2000), "Norcantharidin-induced post-G2/M Apoptosis is Dependent on Wild-Type p53 Gene." Biochem. Biophys. Res. Comm. 276, 278-285.

Honkanan, R.E. et al., (1993), "Cantharidin, another natural toxin that inhibits the activity of serine/threonine protein phosphatases types 1 and 2A." FEBS Lett., 330, 283-286.

Hoshikawa et al. (1994), "Trichostatin A Induces Morphological Changes and Gelsolin Expression by Inhibiting Histone Deacetylase in Human Carcinoma Cell Lines" Exp. Cell Res., 214(1), pp. 189-197.

Huang, L. (2006), "Targeting histone deacetylases for the treatment of cancer and inflammatory diseases", J. Cellular Phys., vol. 209, pp. 611-616.

Hughes et al. (1988), "Ciliary neurotrophic factor induces type-2 astrocyte differentiation in culture." Nature, vol. 335, pp. 70-73.

Joshi, S., et al. (2006), "Retinoic acid receptors and tissue-transglutaminase mediate short-term effect of retinoic acid on migration and invasion of neuroblastoma SH-SY5Y cells." Oncogene, 25:240-274.

Kamitami et al. (2002), "Histone acetylation may suppress human glioma cell proliferation when p21WAF/Cip1 and gelsolin are induced." Neuro-Oncology, Apr. 2002, pp. 95-101.

Kawamura, N. et al. (1990), "Endothall Thioanhydride: Structural Aspects of Unusually High Mouse Toxicity and Specific Binding Site in Liver." Chem. Res. Toxicol., vol. 3, pp. 318-324.

Kelly et al. (2005), "Drug insight: histone deacetylase inhibitors-development of the new targeted anticancer agent suberoylanilide hydroxamic acid." Nature Clinical Practice Oncology, vol. 2, No. 3, pp. 150-157.

Kijima et al. (1993), "Trapoxin, an Antitumor Cyclic Tetrapeptide, Is an Irreversible Inhibitor of Mammalian Histone Deacetylase" J. Biol. Chem., 268(30), pp. 22429-22435.

Kim et al. (1999), "Selective Induction of Cyclin-Dependent Kinase Inhibitors and Their Roles in Cell Cycle Arrest Caused by Trichostatin A, an Inhibitor of Histone Deacetylase" Ann. N.Y. Acad. Sci., 886, pp. 200-203.

Kim et al. (2004), "Susceptibility and radiosensitization of human glioblastoma cells to Trichostatin A, a histone deacetylase inhibitor." Int. J. Radiation Oncology Biol. Phys., vol. 59, No. 4, pp. 1174-1180.

Kitamura et al. (2000), "Histone deacetylase inhibitor but not arsenic trioxide differentiates acute promyelocytic leukaemia cells with t(11,17) in combination with all-trans retinoic acid" Brit. J. Haematol., 108(4), pp. 696-702.

Korzus et al. (2004), "CBP Histone Acetyltransferase Activity Is a Critical Component of Memory Consolidation" Neuron, vol. 42, pp. 961-972.

Kovach, JS, et al. (1985), "Enhancement of the antiproliferative activity of human interferon by polyamine depletion." Cancer Treat. Rep., vol. 69, pp. 97-103.

Kozikowski et al. (2007), "Functional differences in epigenetic modulators-superiority of mercaptoacetamide-based histone deacetylase inhibitors relative to hydroxamates in cortical neuron neuroprotection studies" J. Med. Chem., 50, pp. 3054-3061.

Kurebayashi et al. (2000), "Expression levels of estrogen receptor-a, estrogen receptor-b, coactivators, and corepressors in breast cancer." Clin. Cancer Res., vol. 6, pp. 512-518.

Langley et al. (2008), "Pulse inhibition of histone deacetylases induces complete resistance to oxidative death in cortical neurons without toxicity and reveals a role for cytoplasmic p21wafl/cipl in cell cycle-independent neuroprotection" J. Neurosci., 28(1), pp. 163-176.

Lavinsky et al. (1998), "Diverse signaling pathways modulate nuclear receptor recruitment of N-CoR and SMRT complexes." Proc. Natl. Acad. Sci., vol. 95, pp. 2920-2925.

Levenson et al. (2004), "Regulation of Histone Acetylation during memory formation in the hippocampus" J. Biol. Chem., 29(39), pp. 40545-40559.

Li, X-N., et al. (2005), "Valproic acid induces growth arrest, apoptosis, and senescence in medulloblastomas by increasing histone hyperacetylation and regulating expression of p21Cip1, CDK4, and CMYC." Mol Cancer Ther., 4(12):1912-1922.

Li, Y.M. et al. (1992), "Cantharidin-binding protein: Identification as protein phosphatase 2A." Proc. Natl. Acad. Sci. USA, 89, 11867-11870.

Lin et al (1998), "Role of the histone deacetylase complex in acute promyelocytic leukaemia" Nature, 391(6669), pp. 811-814.

Lu, J. et al. (2008), "LB-1 an inhibitor of serine-threonine protein phosphatase PP2A, suppresses the growth of glioblastoma cells in vitro and in vivo" 99th AACR annual meeting, Abstract #5693.

Lu, Shui-Yu et al. (1993), "Aqueous ring-opening metathesis polymerization and copolymerization of 2, 3-dicarboxylic acid anhydride, 2, 3-bis(methoxymethyl) and 2, 3-dicarboxylic acid monomethyl ester derivatives of 7-oxanorbomene" European Polymer Journal 29(2-3) 269-79.

Lu, Shui-Yu et al. (1994), "Aqueous ring-opening metathesis polymerization of 7-oxanobomene derivatives with oxygen-containing functionalities" Macromolecular Chemistry and Physics 195(4) 1273-88.

Mangan et al. (2007), "Turning back the clock on neurodegeneration" Cell, vol. 129, pp. 851-853.

Manka, Jason T. et al. (2000), "Retro Diels-Alder Reactions of 5,6-Disubstituted-7-oxabicyclo[2.2.1]hept-2-enes: Experimental and Density Functional Theory Studies" Journal of Organic Chemistry 65(17) 5202-5206.

Mardor et al. (2001), "Monitoring Response to Convection-enhanced Taxol delivery in brain tumor patients using diffusion-weighted magnetic resonance imaging" Cancer Res., 61, pp. 4971-4973.

Matsuzawa, M. et al. (1987), "Endothal and Cantharidin Analogues: Relation of Structure to Herbicidal Activity and Mammalian Toxicity," J. Agric. Food Chem., 35 (5), pp. 823-829.

Matthay, KK., et al. (1999) "Treatment of High-Risk Neuroblastoma With Intensive Chemotherapy, Radiotherapy, Autologous Bone Marrow Transplantation, and 13-Cis-Retinoic Acid." N. Engl. J Med.,341:1165-1173.

McCluskey et al. (1996), "Inhibition of Protein Phosphatase 2A by Cantharidin Analogues" Bioorg. Med. Chem. Lett., 6(9), pp. 1025-1028.

McCluskey et al. (2000), "Anhydride Modified Cantharidin Analogues: Synthesis, Inhibition of Protein Phosphatases 1 and 2A and Anticancer Activity" Bioorg. Med. Chem. Lett., 10, pp. 1687-1690.

McCluskey et al. (2000), "Anhydride modified cantharidin analogues. Is ring opening important in the inhibition of protein phosphatase 2A?" Eur. J. Med. Chem., 35, pp. 957-964.

Mielnicki et al. (1999), "Epigenetic regulation of gelsolin expression in human breast cancer cells", Exp. Cell Res., 249(1), pp. 161-176.

Momparlet, RL. (1980), "In vitro systems for evaluation of combination chemotherapy," Pharmacol. Ther., vol. 8, pp. 21-35.

Myers, E. et al. (2005) "Associations and Interactions Between Ets-1 and Ets-2 and Coregulatory Proteins, SRC-1, AIB1 and NCoR in Breast Cancer," Clin. Cancer Res., vol. 11, pp. 2111-2122.

National Library of Medicine, Medical Subject Headings (MeSH): Phosphatases (2009).

Paez et al. (2006), "PI3K/PTEN/AKT pathway." Signal Transduction in Cancer, Kluwer Academic Publishers, vol. 115, pp. 1-28.

Park, DM. et al. (2007) "N-CoR pathway targeting induces glioblastoma derived cancer stem cell differentiation," Cell Cycle, vol. 6, issue 4, pp. 467-470.

Peng, F. et al. (2002), "Induction of apoptosis by norcantharidin in human colorectal cell lines: involvement of the CD95 receptor/ligand," J. Cancer Res. Clin. Oncol., vol. 128, pp. 223-230.

Price et al. (2007), "Histone deacetylase inhibitors: an analysis of recent patenting activity" Expert Opin. Ther. Patents, 17(7), pp. 745-765.

Ramezanian, M. et al. (1989), "A new super-electrophile: alpha-(phenylsulfonyl)malcic anhydride." J. Org. Chem., 54, 2852-2854.

Richon et al. (1998), "A class of hybrid polar inducers of transformed cell differentiation inhibits histone deacetylases" Proc. Natl. Acad. Sci. USA, 95(6), pp. 3003-3007.

Riester et al. (2007), "Histone deacetylase inhibitors-turning epigenic mechanisms of gene regulation into tools of therapeutic intervention in malignant and other diseases" Appl. Microbiol. Biotechnol., vol. 75, pp. 499-514.

Rutka et al. (1988), "Effect of retinoids on the proliferation, morphology and expression of glial fibrillary acidic protein of an anaplastic astrocytoma cell line," Int. J. Cancer, vol. 42, pp. 419-427.

Sahin et al. (2005), "Retinoic Acid Isomers Protect Hippocampal Neurons From Amyloid-beta Induced Neurodegeneration." Neurotoxicity Res., vol. 7(3), pp. 243-250.

Sakoff et al. (2002), "Anticancer activity and protein phosphatase 1 and 2A inhibition of a new generation of cantharidin analogues" Invest. New Drugs, 20, pp. 1-11.

Saito et al. (1999), "A synthetic inhibitor of histone deacetylase, MS-27-275, with marked in vivo antitumor activity against human tumors" Proc. Natl. Acad. Sci. USA, 96(8), pp. 4592-4597.

Sakoff, JA. (2004) "Protein Phosphatase Inhibition: Structure Based Design, Towards New Therapeutic Agents," Current Pharmaceutical Design, vol. 10, pp. 1139-1159.

Sanderson, L et al. (2004), "Plasma Pharmacokinetics and Metabolism of the Histone Deacetylase Inhibitor Trichostatin A after Intraperitoneal Administration to Mice," Drug Metabolism and Disposition, vol. 32, No. 10, pp. 1132-1138.

Science IP Search Report dated Sep. 20, 2007.

Singh et al. (2003), "Identification of a cancer stem cell in human brain tumors," Cancer Research, vol. 63, pp. 5821-5828.

Singh et al. (2004), "Identification of human brain tumour initiating cells," Nature, vol. 432, pp. 396-401.

Smith, W. L., et al. (2002), "Histone deacetylase inhibitors enhance *Candida albicans* sensitivity to azoles and related antifungals: correlation with reduction in CDR and ERG upregulation", Antimicrob. Agents Chemother., 46(11), pp. 3532-3539.

Song et al. (2002), "Synthesis and Biological Properties of Amino Acid Amide Ligand-Based Pyridinioalkanoyl Thioesters as Anti-HIV Agents" Bioorganic and Medicinal Chem., 10(5), pp. 1263-1273.

Stewart et al. (2007), "Synthesis and Biological Evaluation of Norcantharidin Analogues: Towards PP1 Selectivity", Bioorganic & Medicinal Chemistry, vol. 15, pp. 7301-7310.

Stupp et al. (2005), "Radiotherapy plus Concomitant and Adjuvant Temozolomide for Glioblastoma," N. Engl. J. Med., vol. 352, pp. 987-996.

Suzuki et al. (1999), "Synthesis and Histone Deacetylase Inhibitory Activity of New Benzamide Derivatives" J. Med. Chem., 42(15), pp. 3001-3003.

Sweatt, J. D. (2007), "Behavioural neuroscience: Down memory lane" Nature, 447, pp. 151-152.

Tocris Biosciences: retinoic acid receptors product data sheet (2010).

Toma et al. (2005), "Retinoids and human breast cancer: in vivo effects of an antagonist for RAR-α." Cancer Lett., 219, pp. 27-31.

Touma et al. (2005), "Retinoic acid and the histone deacetylase inhibitor Trichostatin A inhibit the proliferation of human renal cell carcinoma in a xenograph tumor model." Clin. Cancer Res., 11(9), pp. 3558-2566.

Uchida et al. (2000), "Direct isolation of human central nervous system stem cells." Proc. Natl. Acad. Sci. USA, vol. 97, pp. 14720-14725.

Valeriote, F. (1975), "Synergistic interaction of anticancer agents: A cellular perspective," Cancer Chemother. Rep., vol. 59, pp. 895-900.

Wang, GS (1983), "Hydrolysis and demethylation of cantharidin on the relief of its urinary irritation," Chin. Pharmac. Bull., col. 18, pp. 18-19, with English language summary.

Wang, GS (1989), "Medical uses of mylabris in ancient China and recent studies," J. Ethnopharmacol., vol. 26, pp. 147-162.

Wang, GS et al. (1986), "Results of clinical trials in 244 cases of primary hepatoma and with norcantharidin," Chinese. Pharm. Bull., vol. 21, pp. 90-93, with English translation of abstract.

Wang, GS et al. (1987), "Effect of norcantharidin on the number of white blood cells," Chinese Pharm. Bull., vol. 22, pp. 517-519, with English translation of abstract.

Warrell, Jr. et al. (1998), "Therapeutic Targeting of Transcription in Acute Promyelocytic Leukemia by Use of an Inhibitor of Histone Deacetylase" J. Natl. Cancer Inst., 90, pp. 1621-1625.

Waters, CE et al. (2004), "Analysis of co-factor 10 function in glucocorticoid-resistant small cell carcinoma line," J. Endocrinol., vol. 183, pp. 375-383.

Weinmann et al. (2005) "Histone deacetylase inhibitors: a survey of recent patents." Expert Opin. Ther. Patents, 15(12), pp. 1677-1690.

Yoshida, M et al. (1990), "Potent and Specific Inhibition of Mammalian Histone Deacetylase Both in vivo and in vitro by Trichostantin A," Journal of Biological Chem., vol. 265, No. 28, pp. 17174-17179.

Yung et al. (1996), "Treatment of recurrent malignant gliomas with high-dose 13-cis-retinoic acid," Clin. Cancer Res. vol. 2, pp. 1931-1935.

Mexican Office Action issued Mar. 25, 2013 in connection with Mexican Patent Application No. MX/a/2011/001007 (including English Language Summary provided by Mexican Agent).

Chinese official action (including English translation thereof) issued Jul. 1, 2013 by the Chinese Patent Office in connection with Chinese Patent Application No. 200880115815.7.

Eurasian Official Action (including English translation thereof) issued Jun. 7, 2013 by the Eurasian Patent Office in connection with Eurasian Patent Application No. 201170288.

Communication pursuant to Art. 94(3)EPC issued Jul. 16, 2013 by the European Patent Office in connection with European Patent Application No. 09803283.2.

* cited by examiner

OXABICYCLOHEPTANES AND OXABICYCLOHEPTENES, THEIR PREPARATION AND USE

This application is a divisional of U.S. Ser. No. 12/460,404, filed Jul. 17, 2009, now U.S. Pat. No. 8,227,473, and claims the benefit of U.S. Provisional Application No. 61/137,691, filed Aug. 1, 2008, the content of both of which in their entirety are hereby incorporated by reference in this application.

Throughout this application, certain publications are referenced. Full citations for these publications may be found immediately preceding the claims. The disclosures of these publications in their entireties are hereby incorporated by reference into this application in order to describe more fully the state-of-the art to which this invention relates.

BACKGROUND OF THE INVENTION

Retinoids, metabolites of vitamin A, have been examined therapeutically against a variety of tumors, including gliomas. (Yung et al. (1996)) Nuclear receptor co-repressor (N-CoR) is closely associated with the retinoid receptor and is released upon ligand binding to the receptor. (Bastien at al. (2004)) By preventing the action of protein phosphatase-1 and protein phosphatase-2A, anti-phosphatases increase the phosphorylated form of N-CoR and promotes its subsequent cytoplasmic translocation. (Hermanson at al. (2002))

The phosphatase inhibitor, Cantharidin, has anti-tumor activity against human cancers of the liver (hepatomas) and of the upper gastrointestinal tract but is toxic to the urinary tract (Wang, 1959).

The publication of a report that cantharidin acts as a protein phosphatase inhibitor prompted a more general interest in compounds with this type of chemical structure (Li and Casida, 1992). Previously, it had been found that the simpler congener and its hydrolysis product (commercially available as the herbicide, Endothall) are hepatotoxic (Graziani and Casida, 1997). Binding studies have shown that the action of certain cantharidin homologs is direct on protein phosphatase-2A and indirect on protein phosphatase-1 (Honkanen at al., 1993; Li et al., 1993).

Despite these successes, few compounds of this type have been screened for anti-tumor or cytotoxic activity. Currently, there is a significant need to develop inhibitors of protein phosphatases that are more active, less toxic and more specific in action than the known substances mentioned above.

SUMMARY OF THE INVENTION

This invention provides a compound having the structure

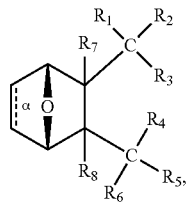

wherein bond α is present or absent; $R_1$ and $R_2$ is each independently H, O$^-$ or OR$_9$, where $R_9$ is H, alkyl, substituted alkyl, alkenyl, alkynyl or aryl, or $R_1$ and $R_2$ together are =O; $R_3$ and $R_4$ are each different, and each is O(CH$_2$)$_{1-6}$R$_9$ or OR$_{10}$, or

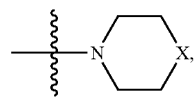

where X is O, S, NR$_{11}$, or N$^+$R$_{11}$R$_{11}$, where each R$_{11}$ is independently H, alkyl, hydroxyalkyl, substituted C$_2$-C$_{12}$ alkyl, alkenyl, substituted C$_4$-C$_{12}$ alkenyl, alkynyl, substituted alkynyl, aryl, substituted aryl where the substituent is other than chloro when R$_1$ and R$_2$ are =O,

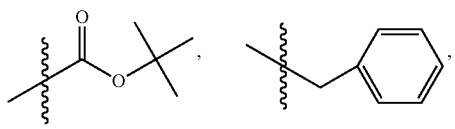

—CH$_2$CN, —CH$_2$CO$_2$R$_{12}$, —CH$_2$COR$_{12}$, —NHR$_{12}$ or —NH$^+$(R$_{12}$)$_2$, where each R$_{12}$ is independently alkyl, alkenyl or alkynyl, each of which is substituted or unsubstituted, or H; where R$_{10}$ is substituted alkyl, substituted alkenyl, substituted alkynyl, or substituted aryl, or R$_3$ and R$_4$ are each different and each is OH or

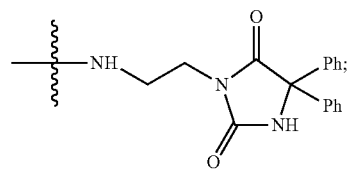 [SMILES: *NCCN1C(=O)NC(c2ccccc2)(c2ccccc2)C1=O]

R$_5$ and R$_6$ is each independently H, OH, or R$_5$ and R$_6$ taken together are =O; and R$_7$ and R$_8$ is each independently H, F, Cl, Br, SO$_2$Ph, CO$_2$CH$_3$, or SR$_{13}$, where R$_{13}$ is H, aryl or a substituted or unsubstituted alkyl, alkenyl or alkynyl, or a salt, enantiomer or zwitterion of the compound.

This invention provides a process for preparing the above compound comprising (a) reacting compounds of the structure

to form an anhydride the structure

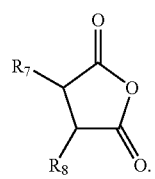

(b) reacting the anhydride having the above structure with at least one nucleophile to form compounds having the structure

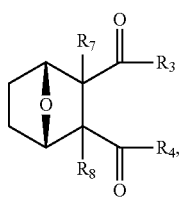

where $R_3$ and $R_4$ are each different, and each is $O(CH_2)_{1-6}R_9$ or $OR_{10}$, or

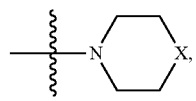

where X is O, S, $NR_{11}$, or $N^+R_{11}R_{11}$, where each $R_{11}$ is independently H, alkyl, hydroxyalkyl, substituted $C_2$-$C_{12}$ alkyl, alkenyl, substituted $C_4$-$C_{12}$ alkenyl, alkynyl, substituted alkynyl, aryl, substituted aryl where the substituent is other than chloro when $R_1$ and $R_2$ are =O,

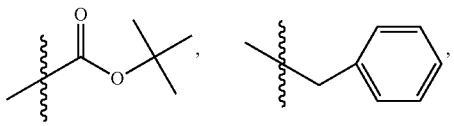

—$CH_2CN$, —$CH_2CO_2R_{12}$, —$CH_2COR_{12}$, —$NHR_{12}$ or —$NH^+(R_{12})_2$, where each $R_{12}$ is independently alkyl, alkenyl or alkynyl, each of which is substituted or unsubstituted, or H; where $R_{10}$ is substituted alkyl, substituted alkenyl, substituted alkynyl, or substituted aryl, or R3 and R4 are each different and each is OH or

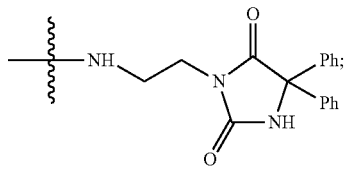 [SMILES: *NCCN1C(=O)NC(c2ccccc2)(c2ccccc2)C1=O]

$R_7$ and $R_8$ is each independently H, F, Cl, Br, $SO_2Ph$, $CO_2CH_3$, or $SR_{13}$, where $R_{13}$ is H, aryl or a substituted or unsubstituted alkyl, alkenyl or alkynyl.

This invention provides a method of controlling undesired vegetation comprising contacting the vegetation or its environment with a herbicidally effective amount of the compounds of this invention.

This invention provides a method of inhibiting plant phosphatase activity comprising contacting the plant or its environment with a herbicidally effective amount of the compounds of this invention.

The invention provides a method of preventing or treating a fungal infection in a subject comprising administering to the subject an effective amount of the compounds of this invention.

This invention provides a method of treating a subject with a neurodegenerative disease comprising administering to the subject an effective amount any of the compounds of this invention, thereby treating the subject.

This invention provides a method for reducing the amount of GSK-3β in a cell comprising contacting the cell with an effective amount of any of the compounds of this invention so as to thereby reduce the amount of GSK-3β in the cell.

This invention provides a method for increasing the amount of phosphorylated Akt in a cell comprising contacting the neural cell with an effective amount of any of the compounds of this invention, so as to thereby increase the amount of phosphorylated Akt in the cell.

This invention provides a method for reducing the phosphorylation of Tau in cell, comprising contacting the cell with an effective amount of any of the compounds of this invention, so as to thereby reduce the phosphorylation of Tau in the cell.

This invention provides a method for reducing the aggregation of Tau in a cell, comprising contacting the cell with an effective amount of any of the compounds of this invention, so as to thereby reduce the phosphorylation of Tau in the cell.

DETAILED DESCRIPTION OF THE INVENTION

Figure 1:
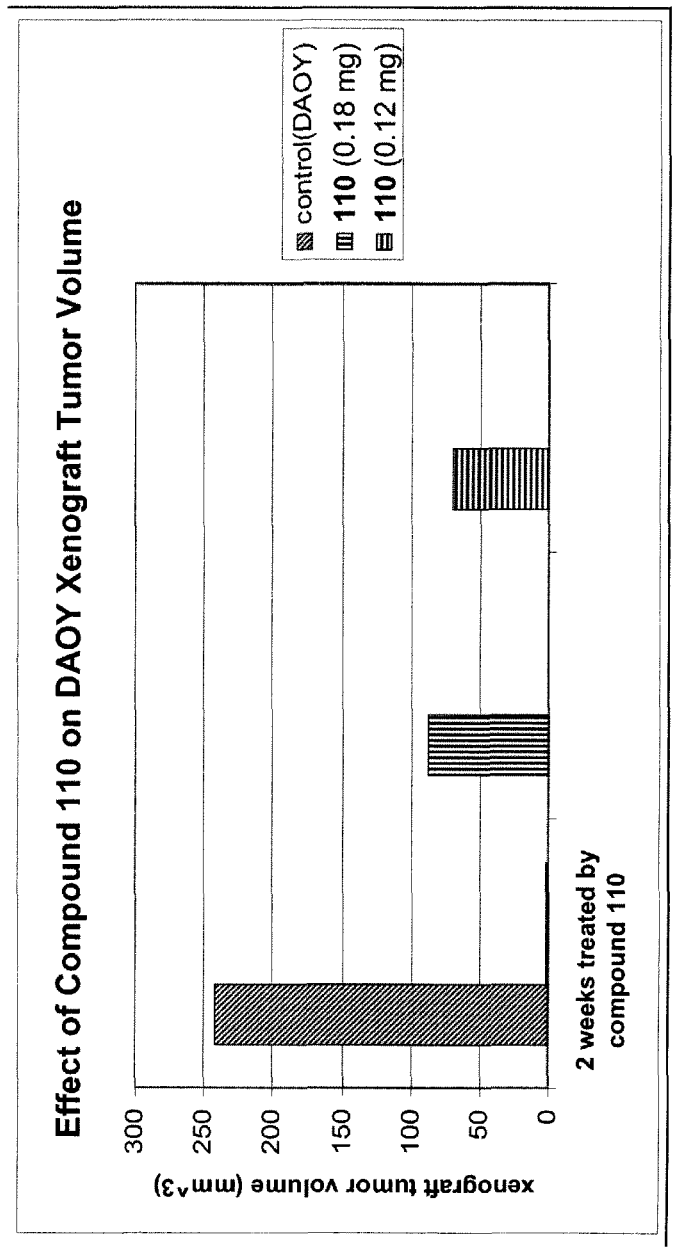
FIG. 1: Compound 110 inhibition of DAOY xenografts
Medulloblastoma DAOY cells were implanted subcutaneously in the flanks of SCID mice. After 7 days when the implanted tumor cells reached a mass with the average diameter of 6 mm, 6 animals received 0.12 mg of Compound 110, 6 animals received 0.18 mg of Compound 110, and 6 animals, received vehicle (PBS) only. After two weeks of treatment all animals were sacrificed, the subcutaneous tumor masses resected, and their volumes calculated. Both doses of drugs led to significant inhibition of tumor growth.

This invention provides a compound having the structure

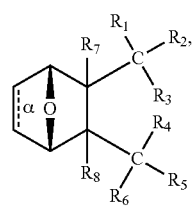

wherein
bond α is present or absent;
$R_1$ and $R_2$ is each independently H, O⁻ or $OR_9$, where $R_9$ is H, alkyl, substituted alkyl, alkenyl, alkynyl or aryl,
or $R_1$ and $R_2$ together are =O;
$R_3$ and $R_4$ are each different, and each is $O(CH_2)_{1-6}R_9$ or $OR_{10}$, or

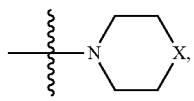

where X is O, S, $NR_{11}$, or $N^+R_{11}R_{11}$,
where each $R_{11}$ is independently H, alkyl, hydroxyalkyl, substituted $C_2$-$C_{12}$ alkyl, alkenyl, substituted $C_4$-$C_{12}$ alkenyl, alkynyl, substituted alkynyl, aryl, substituted aryl where the substituent is other than chloro when $R_1$ and $R_2$ are =O,

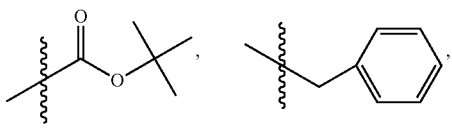

—$CH_2CN$, —$CH_2CO_2R_{12}$, $CH_2COR_{12}$, —$NHR_{12}$ or —$NH^+(R_{12})_2$,
where each $R_{12}$ is independently alkyl, alkenyl or alkynyl, each of which is substituted or unsubstituted, or H;
where $R_{10}$ is substituted alkyl, substituted alkenyl, substituted alkynyl, or substituted aryl,
or R3 and R4 are each different and each is OH or

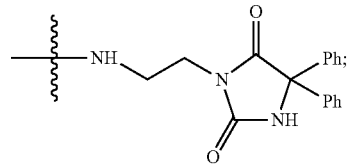 [SMILES: *NCCN1C(=O)NC(c2ccccc2)(c2ccccc2)C1=O]

$R_5$ and $R_6$ is each independently H, OH, or $R_5$ and $R_6$ taken together are =O; and
$R_7$ and $R_8$ is each independently H, F, Cl, Br, $SO_2Ph$, $CO_2CH_3$, or $SR_{13}$,
where $R_{13}$ is H, aryl or a substituted or unsubstituted alkyl, alkenyl or alkynyl,
or a salt, enantiomer or zwitterion of the compound.
In one embodiment, the above compound has the structure

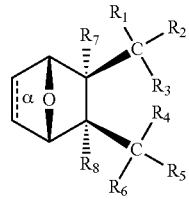

In one embodiment bond α is present. In another embodiment bond α is absent.
In one embodiment of the above compound
$R_3$ is $OR_9$ or $O(CH_2)_{1-6}R_{10}$,
where $R_9$ is aryl or substituted ethyl;

where $R_{10}$ is substituted phenyl, wherein the substituent is in the para position;
$R_4$ is

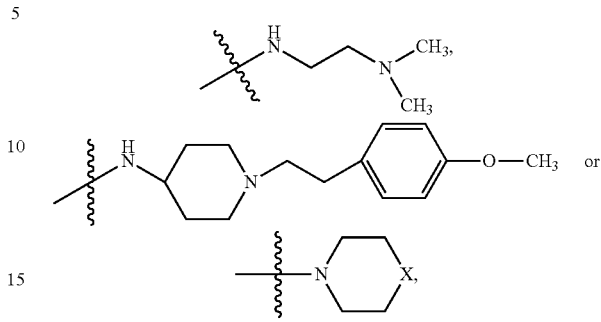

where X is O, S, $NR_{11}$, or $N^+R_{11}R_{11}$,
where each $R_{11}$ is independently H, alkyl, hydroxyalkyl, substituted $C_2$-$C_2$ alkyl, alkenyl, substituted $C_4$-$C_{12}$ alkenyl, alkynyl, substituted alkynyl, aryl, substituted aryl where the substituent is other than chloro,

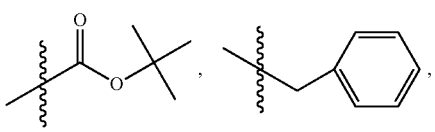

—$CH_2CN$, —$CH_2CO_2R_{12}$, —$CH_2COR_{12}$, —$NHR_{12}$ or —$NH^+(R_{12})_2$,
where $R_{12}$ is alkyl, alkenyl or alkynyl, each of which is substituted or unsubstituted, or H;
or where $R_3$ is OH and $R_4$ is

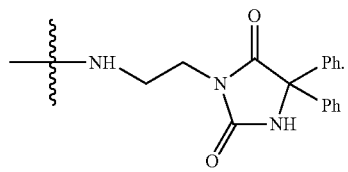 [SMILES: *NCCN1C(=O)NC(c2ccccc2)(c2ccccc2)C1=O]

In another embodiment of the above invention $R_4$

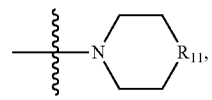

where $R_{11}$ is alkyl or hydroxylalkyl; or $R_4$ is

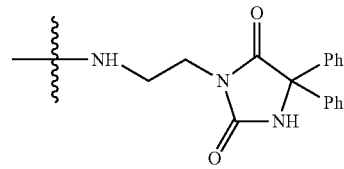 [SMILES: *NCCN1C(=O)NC(c2ccccc2)(c2ccccc2)C1=O]

when $R_3$ is OH.
In another embodiment of the above compound,
$R_1$ and $R_2$ together are =O;

$R_3$ is $OR_9$ or $OR_{10}$ or $O(CH_2)_{1-2}R_9$,
  where $R_9$ is aryl or substituted ethyl;
  where $R_{10}$ is substituted phenyl, wherein the substituent is in the para position;
or $R_3$ is OH and $R_4$ is

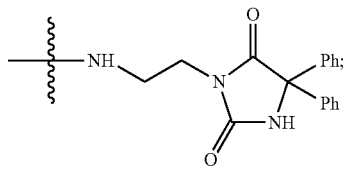 [SMILES: *NCCN1C(=O)NC(c2ccccc2)(c2ccccc2)C1=O]

$R_4$ is

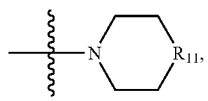

where $R_{11}$ is alkyl or hydroxyl alkyl;
$R_5$ and $R_6$ together are =O; and
$R_7$ and $R_8$ are each independently H.
In another embodiment of the above compounds,
$R_1$ and $R_2$ together are =O;
$R_3$ is OH, $O(CH_2)R_9$, or $OR_{10}$,
  where $R_9$ is phenyl;
  where $R_{10}$ is $CH_2CCl_3$,

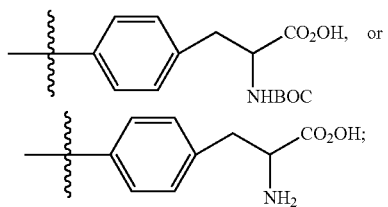

$R_4$ is

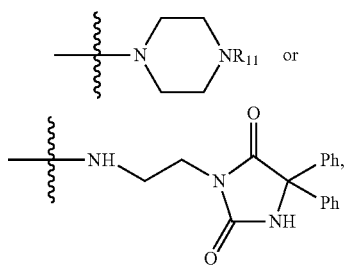

where $R_{11}$ is $CH_3$ or $CH_3CH_2OH$;
$R_5$ and $R_6$ together are =O; and
$R_7$ and $R_8$ are each independently H.
In one embodiment, $R_3$ is $OR_{10}$, where $R_{10}$ is $(CH_2)_{1-6}(CHNHBOC)CO_2H$, $(CH_2)_{1-6}(CHNH_2)CO_2H$, or $(CH_2)_{1-6}CCl_3$,
In another embodiment, $R_{10}$ is $CH_2(CHNHBOC)CO_2H$. In a further embodiment, $R_{10}$ is $CH_2CCl_3$.
In one embodiment of the above compounds, $R_3$ is $O(CH_2)_{1-6}R_9$ where $R_9$ is phenyl.

In another embodiment of the above compounds, $R_3$ is $O(CH_2)R_9$ where R9 is phenyl.
In an embodiment of the above compounds $R_3$ is OH and $R_4$ is

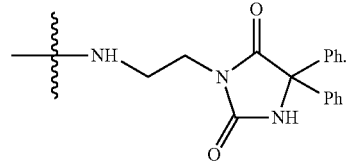 [SMILES: *NCCN1C(=O)NC(c2ccccc2)(c2ccccc2)C1=O]

In another embodiment of the above compounds, $R_4$ is

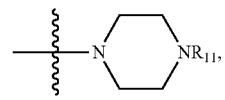

wherein $R_{11}$ is hydroxyalkyl.
In another embodiment of the above compound, $R_{11}$ is —$CH_2CH_2OH$.
In an embodiment of the above compound, $R_4$ is

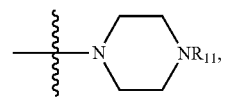

wherein $R_{11}$ is alkyl. In further embodiment, $R_{11}$ is —CH3.
In another embodiment of the above compounds $R_4$ is wherein $R_4$ is

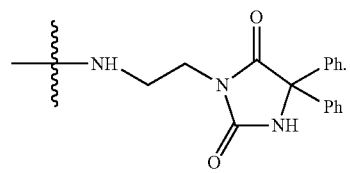 [SMILES: *NCCN1C(=O)NC(c2ccccc2)(c2ccccc2)C1=O]

In an embodiment, the compound has the structure (compound 109)

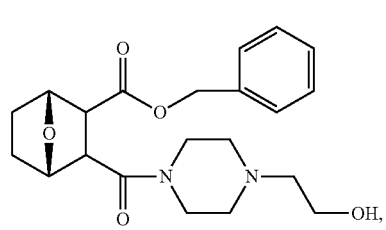

(compound 110)

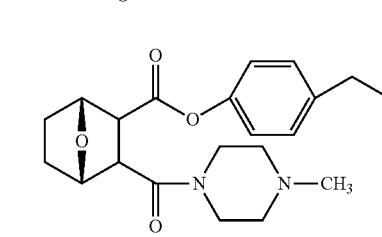

(compound 112)

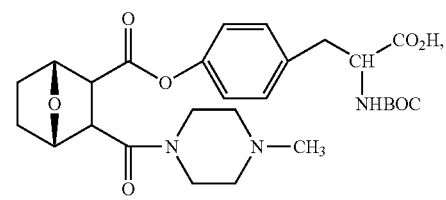

(compound 113)

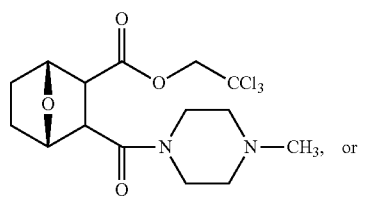

(compound 114)

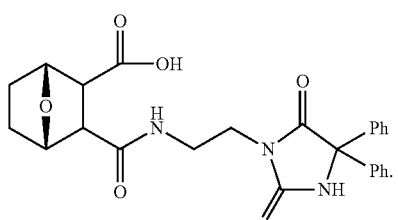

In another embodiment, the compound has the structure (compound 109E)

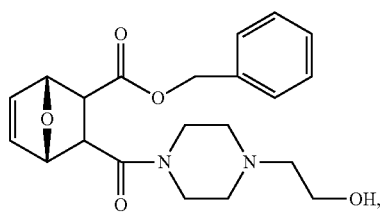

(compound 110E)

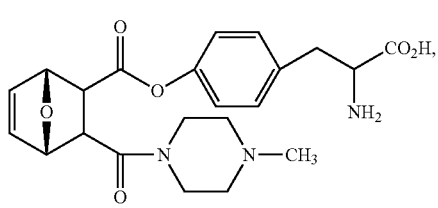

(compound 112E)

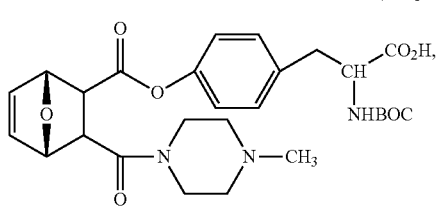

(compound 113E)

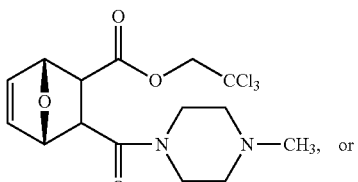

(compound 114E)

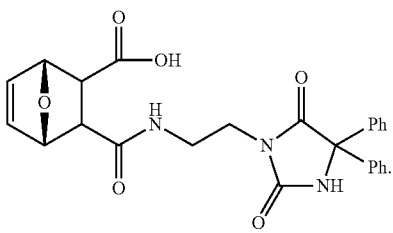

This invention provides a pharmaceutical composition comprising any of the above described compounds and a pharmaceutically acceptable carrier.

This invention provides a process for preparing any of the above compounds comprising (a) reacting compounds of the structure

to form an anhydride the structure

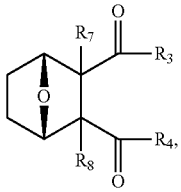

(b) reacting the anhydride having the above structure with at least one nucleophile to form compounds having the structure

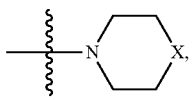

where
$R_3$ and $R_4$ are each different, and each is $O(CH_2)_{1-6}R_9$ or $OR_{10}$, or where X is O, S, $NR_{11}$, or $N^+R_{11}R_{11}$, where each $R_{11}$ is independently H, alkyl, hydroxyalkyl, substituted $C_2$-$C_{12}$ alkyl, alkenyl, substituted $C_4$-$C_{12}$ alkenyl, alkynyl, substituted alkynyl, aryl, substituted aryl where the substituent is other than chloro when $R_1$ and $R_2$ are =O,

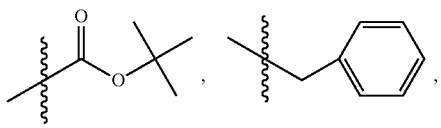

—$CH_2CN$, —$CH_2CO_2R_{12}$, —$CH_2COR_{12}$, —$NHR_{12}$ or —$NH^+(R_{12})_2$, where each $R_{12}$ is independently alkyl, alkenyl or alkynyl, each of which is substituted or unsubstituted, or H;

where $R_{10}$ is substituted alkyl, substituted alkenyl, substituted alkynyl, or substituted aryl, or $R_3$ and $R_4$ are each different and each is OH or

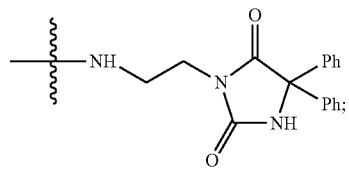 [SMILES: *NCCN1C(=O)NC(c2ccccc2)(c2ccccc2)C1=O]

$R_7$ and $R_8$ is each independently H, F, Cl, Br, $SO_2Ph$, $CO_2CH_3$, or $SR_{13}$, where $R_{13}$ is H, aryl or a substituted or unsubstituted alkyl, alkenyl or alkynyl.

In one embodiment of the above process, the nuclephile comprises at least one hydroxyl group. In another embodiment, the nucleophile is $O(CH_2)_{1-6}R_9$ or $OR_{10}$, wherein $R_9$ and $R_{10}$ are as described above.

In another embodiment, the nucleophile comprises at least one free amine group. In a further embodiment the nucleophile is

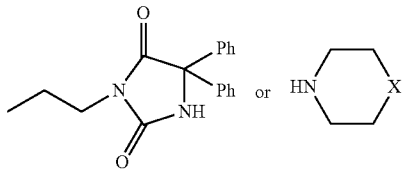

where X is as described herein.

In another embodiment, the above process further comprises (c) reacting the product of step (b) with hydrogen in the presence of a catalyst to form a compound having the structure

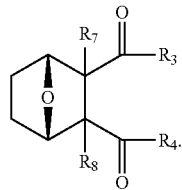

The compounds disclosed hereinabove may be used in a method of controlling undesired vegetation comprising contacting the vegetation or its environment with a herbicidally effective amount of the compounds of any one of invention.

The compounds disclosed hereinabove may also be used in method of inhibiting plant phosphatase activity comprising contacting the plant or its environment with a herbicidally effective amount of the compounds of any one of the invention.

The compounds disclosed herein above may be used in a method of preventing or treating a fungal infection in a subject comprising administering to the subject an effective amount of the compounds of the invention to treat the fungal infection, thereby treating the fungal infection.

The compounds disclosed herein maybe used in a method of treating a subject afflicted with breast cancer, colon cancer, large cell lung cancer, adenocarcinoma of the lung, small cell lung cancer, stomach cancer, liver cancer, ovary adenocarcinoma, pancreas carcinoma, prostate carcinoma, promylocytic leukemia, chronic myelocytic leukemia, or acute lymphocytic leukemia, comprising administering to the subject a therapeutically effective amount of the compounds of the invention, thereby treating the subject.

The compounds disclosed herein may be used in a method of treating a subject with a neurodegenerative disease comprising administering to the subject an effective amount any of the compounds of the invention, thereby treating the subject.

The compounds disclosed herein may be used in a method for reducing the amount of GSK-3β in a cell comprising contacting the cell with an effective amount of any of the compounds of the invention so as to thereby reduce the amount of GSK-3β in the cell.

The compounds disclosed herein may be used in a method for increasing the amount of phosphorylated Akt in a cell comprising contacting the neural cell with an effective amount of any of the compounds of the invention, so as to thereby increase the amount of phosphorylated Akt in the cell.

The compounds disclosed herein may be used in a method for reducing the phosphorylation of Tau in cell, comprising contacting the cell with an effective amount of any of the compounds of the invention, so as to thereby reduce the phosphorylation of Tau in the cell.

The compounds disclosed herein may be used in a method for reducing the aggregation of Tau in a cell, comprising contacting the cell with an effective amount of any of the compounds of the invention, so as to thereby reduce the phosphorylation of Tau in the cell.

The compounds of the invention may also be used in a method of inhibiting proliferation of a cancer cell which does not overexpress N-CoR comprising administering to the subject any of the compounds of the invention in an amount to inhibit proliferation of the cancer cell.

The compounds of the invention may also be used in a method of inhibiting proliferation of a cancer cell which overexpresses TCTP comprising administering to the subject any of the compound of the invention in an amount effective to inhibit proliferation of the cancer cell.

In the above described methods, the cancer may be adrenocortical cancer, bladder cancer, osteosarcoma, cervical cancer, esophageal, gallbladder, head and neck cancer, Hodgkin lymphoma, non-Hodgkin lymphoma, renal cancer, melanoma, pancreatic cancer, rectal cancer, thyroid cancer and throat cancer.

In the method of the invention, the histone deacetylase ligand may be an inhibitor, e.g. the histone deacetylase inhibitor of HDAC-3 (histone deacetylase-3). The histone deacetylase ligand may also be selected from the group consisting of 2-amino-8-oxo-9,10-epoxy-decanoyl, 3-(4-aroyl-1H-pyrrol-2-yl)-N-hydroxy-2-propenamide, APHA Compound 8, apicidin, arginine butyrate, butyric acid, depsipeptide, depudecin, HDAC-3, m-carboxycinnamic acid bis-hydroxamide, N-(2-aminophenyl)-4-[N-(pyridin-3-ylmethoxycarbonyl) aminomethyl]benzamide, MS 275, oxamfiatin, phenylbutyrate, pyroxamide, scriptaid, sirtinol, sodium butyrate, suberic bishydroxamic acid, suberoylanilide hydroxamic acid, trichostatin A, trapoxin A, trapoxin 9 and valproic acid.

The compounds of this invention may be used in combination with compounds which inhibit the enzyme histone deacetylase (HDAC). These HDAC enzymes post-translationally modify histones (U.S. Patent Publication No. 2004/0197888, Armour et al.) Histones are groups of proteins which associate with DNA in eukaryotic cells to form compacted structures called chromatin. This compaction allows an enormous amount of DNA to be located within the nucleus of a eukaryotic cell, but the compact structure of chromatin restricts the access of transcription factors to the DNA. Acetylation of the histones decreases the compaction of the chromatin allowing transcription factors to bind to the DNA. Deacetylation, catalysed by histone deacetylases (HDACs), increases the compaction of chromatin, thereby reducing transcription factor accessibility to DNA. Therefore, inhibitors of histone deacetylases prevent the compaction of chromatin, allowing transcription factors to bind to DNA and increase expression of the genes.

The invention further contemplates the use of prodrugs which are converted in vivo to the compounds of the invention (see, e.g., R. B. Silverman, 1992, "The Organic Chemistry of Drug Design and Drug Action", Academic Press, Chapter 8, the entire contents of which are hereby incorporated by reference). Such prodrugs can be used to alter the biodistribution (e.g., to allow compounds which would not typically enter a reactive site) or the pharmacokinetics of the compound.

The compounds described in the present invention are in racemic form or as individual enantiomers. The enantiomers can be separated using known techniques, such as those described, for example, in Pure and Applied Chemistry 69, 1469-1474, (1997) IUPAC.

As used herein, "zwitterion" means a compound that is electrically neutral but carries formal positive and negative charges on different atoms. Zwitterions are polar, have high solubility in water and have poor solubility in most organic solvents.

The compounds disclosed herein may also form zwitterions. For example, a compound having the structure

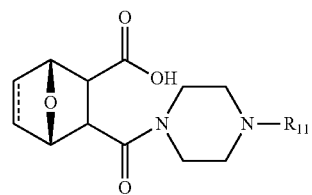

may also form the following zwitterionic structure

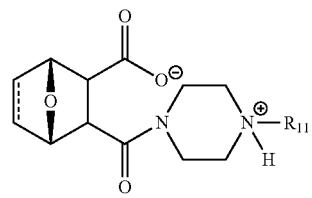

where $R_{11}$ is as defined throughout the disclosures herein.

"Solvent" as used herein is intended to include compounds such as, hexanes, benzene, toluene, diethyl ether, chloroform, methylene chloride, ethyl acetate, 1,4-dioxane, water, THF, acetone, acetonitrile, DMF, DMSO, acetic acid, n-butanol, isopropanol, n-propanol, ethanol, methanol, formic acid, carbon tetrachloride, benzenethiol, chlorobenzene, cyclohexanethiol, 1-diethylaminoethanol, ethylene dichloride, ethylene glycol, xylene, 1,1,2,2-tetrachloroethane, phenol, acetic acid, 1-butanol, 2-butanol, 2-butanone, diglyme, dimethylether, dioxane, petroleum ether, (NMP) N-methyl-2-pyrrolidinone, heptane, glycerin, HMPA(Hexamethylphosphorus triamide), MTBE (methyl t-butyl ether), nitromethane, pyridine, 1-propanol, 2-propanol, and triethylamine.

Certain embodiments of the disclosed compounds can contain a basic functional group, such as amino or alkylamino, and are thus capable of forming pharmaceutically acceptable salts with pharmaceutically acceptable acids, or contain an acidic functional group and are thus capable of forming pharmaceutically acceptable salts with bases. The instant compounds therefore may be in a salt form. As used herein, a "salt" is a salt of the instant compounds which has been modified by making acid or base salts of the compounds. The salt may be pharmaceutically acceptable. Examples of pharmaceutically acceptable salts include, but are not limited to, mineral or organic acid salts of basic residues such as amines; alkali or organic salts of acidic residues such as phenols. The salts can be made using an organic or inorganic acid. Such acid salts are chlorides, bromides, sulfates, nitrates, phosphates, sulfonates, formates, tartrates, maleates, malates, citrates, benzoates, salicylates, ascorbates, and the like. Phenolate salts are the alkaline earth metal salts, sodium, potassium or lithium. The term "pharmaceutically acceptable salt" in this respect, refers to the relatively non-toxic, inorganic and organic acid or base addition salts of compounds of the present invention. These salts can be prepared in situ during the final isolation and purification of the compounds of the invention, or by separately reacting a purified compound of the invention in its free base or free acid form with a suitable organic or inorganic acid or base, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. For a description of possible salts, see, e.g., Berge et al. (1977) "Pharmaceutical Salts", *J. Pharm. Sci.* 66:1-19.

As used herein, "therapeutically effective amount" means an amount sufficient to treat a subject afflicted with a disease (e.g. cancer or a neurodegenerative disease) or to alleviate a symptom or a complication associated with the disease.

As used herein, "herbicidally effective" means an amount sufficient to adversely affect plant growth, particularly through inhibition of plant phosphatase 2 A activity.

As used herein, "treating" means slowing, stopping or reversing the progression of a disease, particularly cancer or a neurodegenerative disease.

As used herein, a "neurodegenerative disease" refers to a disease in which degeneration occurs of either gray or white matter, or both, of the nervous system. Thus, such a disease can be diabetic neuropathy, senile dementias, Alzheimer's disease, Mild Cognitive Impairment (MCI), dementia, Lewy Body Dementia, Frontal Temporal Lobe dementia, Parkinson's Disease, facial nerve (Bell's) palsy, glaucoma, Huntington's chorea, amyotrophic lateral sclerosis (ALS), status epilepticus, non-arteritic optic neuropathy, intervertebral disc herniation, vitamin deficiency, prion diseases such as Creutzfeldt-Jakob disease, carpal tunnel syndrome, peripheral neuropathies associated with various diseases, including but not limited to, uremia, porphyria, hypoglycemia, Sjorgren Larsson syndrome, acute sensory neuropathy, chronic ataxic neuropathy, biliary cirrhosis, primary amyloidosis, obstructive lung diseases, acromegaly, malabsorption syndromes, polycythemia vera, IgA and IgG gammapathies, complications of various drugs (e.g., metronidazole) and toxins (e.g., alcohol or organophosphates), Charcot-Marie-Tooth disease, ataxia telangectasia, Friedreich's ataxia, amyloid polyneuropathies, adrenomyeloneuropathy, Giant axonal neuropathy, Refsum's disease, Fabry's disease and lipoproteinemia.

As used herein, "tauopathies" refers to a class of neurodegenerative diseases which result from aggregation of tau protein in neurofibrillary tangles. Examples of tauopathies include, but are not limited to, Alzheimer's disease, Frontotemporal dementia (Pick's disease), Progressive Supranuclear Palsy, and Corticobasal degeneration.

As used herein, "alkyl" is intended to include both branched and straight-chain saturated aliphatic hydrocarbon groups having the specified number of carbon atoms. Thus, $C_1$-$C_n$ as in "$C_1$-$C_n$ alkyl" is defined to include groups having 1, 2, . . . , n-1 or n carbons in a linear or branched arrangement, and specifically includes methyl, ethyl, propyl, butyl, pentyl, hexyl, and so on. An embodiment can be $C_1$-$C_{12}$ alkyl. "Alkoxy" represents an alkyl group as described above attached through an oxygen bridge. "Hydroxyalkyl" represents an alkyl group as described aboved with a hydroxyl group. Hydroxyalky groups include, for example, $(CH_2)_{1-10}H$ and includes $CH_2OH$, $CH_2CH_2OH$, $CH_2CH_2CH_2OH$ and so forth.

The term "alkenyl" refers to a non-aromatic hydrocarbon radical, straight or branched, containing at least 1 carbon to carbon double bond, and up to the maximum possible number of non-aromatic carbon-carbon double bonds may be present. Thus, $C_2$-$C_n$ alkenyl is defined to include groups having 1, 2, . . . , n-1 or n carbons. For example, "$C_2$-$C_6$ alkenyl" means an alkenyl radical having 2, 3, 4, 5, or 6 carbon atoms, and at least 1 carbon-carbon double bond, and up to, for example, 3 carbon-carbon double bonds in the case of a $C_6$ alkenyl, respectively. Alkenyl groups include ethenyl, propenyl, butenyl and cyclohexenyl. As described above with respect to alkyl, the straight, branched or cyclic portion of the alkenyl group may contain double bonds and may be substituted if a substituted alkenyl group is indicated. An embodiment can be $C_2$-$C_{12}$ alkenyl.

The term "alkynyl" refers to a hydrocarbon radical straight or branched, containing at least 1 carbon to carbon triple bond, and up to the maximum possible number of non-aromatic carbon-carbon triple bonds may be present. Thus, $C_2$-$C_n$ alkynyl is defined to include groups having 1, 2, . . . , n-1 or n carbons. For example, "$C_2$-$C_6$ alkynyl" means an alkynyl radical having 2 or 3 carbon atoms, and 1 carbon-carbon triple bond, or having 4 or 5 carbon atoms, and up to 2 carbon-carbon triple bonds, or having 6 carbon atoms, and up to 3 carbon-carbon triple bonds. Alkynyl groups include ethynyl, propynyl and butynyl. As described above with respect to alkyl, the straight or branched portion of the alkynyl group may contain triple bonds and may be substituted if a substituted alkynyl group is indicated. An embodiment can be a $C_2$-$C_n$ alkynyl.

As used herein, "aryl" is intended to mean any stable monocyclic or bicyclic carbon ring of up to 10 atoms in each ring, wherein at least one ring is aromatic. Examples of such aryl elements include phenyl, naphthyl, tetrahydro-naphthyl, indanyl, biphenyl, phenanthryl, anthryl or acenaphthyl. In cases where the aryl substituent is bicyclic and one ring is non-aromatic, it is understood that attachment is via the aromatic ring. The substituted aryls included in this invention include substitution at any suitable position with amines, substituted amines, alkylamines, hydroxys and alkylhydroxys, wherein the "alkyl" portion of the alkylamines and alkylhydroxys is a $C_2$-$C_n$ alkyl as defined hereinabove. The substituted amines may be substituted with alkyl, alkenyl, alkynl, or aryl groups as hereinabove defined.

The alkyl, alkenyl, alkynyl, and aryl substituents may be substituted or unsubstituted, unless specifically defined otherwise. For example, a ($C_1$-$C_6$)alkyl may be substituted with one or more substituents selected from OH, oxo, halogen, which includes F, Cl, Br, and I, alkoxy, dialkylamino, or heterocyclyl, such as morpholinyl, piperidinyl, and so on.

In the compounds of the present invention, alkyl, alkenyl, and alkynyl groups can be further substituted by replacing one or more hydrogen atoms by non-hydrogen groups described herein to the extent possible. These include, but are not limited to, halo, hydroxy, mercapto, amino, carboxy, cyano and carbamoyl.

The term "substituted" as used herein means that a given structure has a substituent which can be an alkyl, alkenyl, or aryl group as defined above. The term shall be deemed to include multiple degrees of substitution by a named substitutent. Where multiple substituent moieties are disclosed or claimed, the substituted compound can be independently substituted by one or more of the disclosed or claimed substituent moieties, singly or plurally. By independently substituted, it is meant that the (two or more) substituents can be the same or different.

As used herein, "administering" an agent may be performed using any of the various methods or delivery systems well known to those skilled in the art. The administering can be performed, for example, orally, parenterally, intraperitoneally, intravenously, intraarterially, transdermally, sublingually, intramuscularly, rectally, transbuccally, intranasally, liposomally, via inhalation, vaginally, intraoccularly, via local delivery, subcutaneously, intraadiposally, intraarticularly, intrathecally, into a cerebral ventricle, intraventicularly, intratumorally, into cerebral parenchyma or iritraparenchymally.

The following delivery systems, which employ a number of routinely used pharmaceutical carriers, may be used but are only representative of the many possible systems envisioned for administering compositions in accordance with the invention.

Injectable drug delivery systems include solutions, suspensions, gels, microspheres and polymeric injectables, and can comprise excipients such as solubility-altering agents (e.g., ethanol, propylene glycol and sucrose) and polymers (e.g., polycaprylactones and PLGA's).

Implantable systems include rods and discs, and can contain excipients such as PLGA and polycaprylactone.

Oral delivery systems include tablets and capsules. These can contain excipients such as binders (e.g., hydroxypropylmethylcellulose, polyvinyl pyrilodone, other cellulosic materials and starch), diluents (e.g., lactose and other sugars, starch, dicalcium phosphate and cellulosic materials), disintegrating agents (e.g., starch polymers and cellulosic materials) and lubricating agents (e.g., stearates and talc).

Transmucosal delivery systems include patches, tablets, suppositories, pessaries, gels and creams, and can contain excipients such as solubilizers and enhancers (e.g., propylene glycol, bile salts and amino acids), and other vehicles (e.g., polyethylene glycol, fatty acid esters and derivatives, and hydrophilic polymers such as hydroxypropylmethylcellulose and hyaluronic acid).

Dermal delivery systems include, for example, aqueous and nonaqueous gels, creams, multiple emulsions, microemulsions, liposomes, ointments, aqueous and nonaqueous solutions, lotions, aerosols, hydrocarbon bases and powders, and can contain excipients such as solubilizers, permeation enhancers (e.g., fatty acids, fatty acid esters, fatty alcohols and amino acids), and hydrophilic polymers (e.g., polycarbophil and polyvinylpyrolidone). In one embodiment, the pharmaceutically acceptable carrier is a liposome or a transdermal enhancer.

Solutions, suspensions and powders for reconstitutable delivery systems include vehicles such as suspending agents (e.g., gums, zanthans, cellulosics and sugars), humectants (e.g., sorbitol), solubilizers (e.g., ethanol, water, PEG and propylene glycol), surfactants (e.g., sodium lauryl sulfate, Spans, Tweens, and cetyl pyridine), preservatives and antioxidants (e.g., parabens, vitamins E and C, and ascorbic acid), anti-caking agents, coating agents, and chelating agents (e.g., EDTA).

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results.

Discussion

Cantharidin has anti-tumor activity against human cancers of the liver (hepatomas) and of the upper gastrointestinal tract but is toxic to the urinary tract (Wang, 1989). Norcantharidin, a demethylated cantharidin, maintains antitumor activity of cantharidin against hepatomas and cancers of the stomach and esophagus, but has little or no urinary tract toxicity. Norcantharidin also stimulates white blood cell production in patients and mice, a phenomenon not understood mechanistically, but a pharmacological effect of potential benefit as an anticancer agent (Wang et al., 1986; Wang, 1989).

The publication of a report that cantharidin acts as a protein phosphatase inhibitor prompted a more general interest in compounds with this type of chemical structure (Li and Casida, 1992). Previously, it had been found that the simpler congener and its hydrolysis product (commercially available as the herbicide, Endothall) are hepatoxic (Graziano and Casida, 1997). The primary targets in liver appear to be the protein phosphatases PP2A and PP1, all of the compounds showing $ED_{50}$ values at the micromolar level. Binding studies have shown that the action of certain cantharidin homologs is direct on PP2A and indirect on PP1 (Bonkanen et al., 1993; Li et al., 1993). Phosphatase PP1B is affected only at millimolar levels of these compounds, whereas the enzyme PP2C is not influenced at all.

In the past, several cantharidin analogues had been synthesized and evaluated for anti-phosphatase activity and for their ability to inhibit the growth of cancer cells in culture (Sakoff and McClusky, 2004; Hart et al., 2004). Some of the previously evaluated modified norcantharidin molecules inhibited the growth of several human tumor cell lines. The activity of norcantharidin analogues against cells of tumors overexpressing N-CoR or the activity of norcantharidins combined with other potential anti-tumor agents was not analyzed. Further studies included 16 "modified norcantharidins" evaluated for activity against four human tumor cell lines including ovarian, kidney, colorectal and lung as well as a mouse leukemia line. None were as active as single agents as cantharidin or norcantharidin and none were evaluated for activity in combination with another antitumor agent (McCluskey et al., US Patent Application Publication No. 2006/0030616, 2006).

A different series of cantharidin analogues had been previously synthesized and evaluated as pesticides and for anti-tumor activity against cancer cell lines. Forty-three analogues of endothal and cantharidin have been developed and assessed for their activity as herbicides and their lethality to mice (Matsuzawa at al., 1987). Endothal thioanhydride was shown to be a more potent herbicide than endothal but was toxic to the liver of mice (Matsuzawa et al., 1987; Kawamura at al., 1990).

More recently, it has been found that endothal thioanhydride is an active agent against PP2A and PP1 in vivo (Erdodi at al., 1995). Endothal and endothal thioanhydride, like cantharidin, inhibit the activity of PP2A and to some extent, the activity of PP1 (Erdodi et al., 1995). In the liver, the principal target appears to be PP1. In fibroblasts, only endothal thioanhydride caused marked morphological changes whereas cantharidin and endothal did not (Erdodi at al., 1995). The enhanced activity of endothal thioanhydride in vivo is thought to be related to its enhanced lipophilicity resulting in increased diffusion across the plasmalemma (Essers et al., 2001). A more recent publication has described the synthesis of the mono-, and the di-fluoro analogues of Endothal and also the corresponding anhydrides, however no pharmacological data accompanied this synthetic work (Essers et al., 2001).

In pursuing the development of new drug substances in this area, we have found it essential to develop inhibitors that have greater specificity, especially towards those enzymes which display high activity against the replication processes of cancer cells. High specificity also holds out the possibility of avoiding targets important to normal cell function. From the point of view of the physical characteristics of any newly-developed drug substance, it must preeminently have good membrane permeability (i.e., has a log P value of between 2 and 4 units).

The compounds described herein have an antagonistic effect on phosphatase-2A and phosphatase 1. In addition, compounds 110, 112, 113 and 114 each have properties that enhance their entry into the brain.

Endothal is also known as an active defoliant and potent contact herbicide used in many agricultural situations. It is considered effective as a pre-harvest desiccant and as a selective pre-emergence herbicide (Crafts, 1953).

Endothal, norcantharidins and cantharidin are all well known inhibitors of mammalian protein phosphatase as well as potent herbicides (Matsuzawa et al., 1987). The mechanism by which endothal and other homologs exert their potent herbicidal activity has not been studied extensively despite the widespread use of endothal internationally in agriculture. It should be noted that endothal is water soluble where cantharidin and norcantharidin are not.

It was assumed that the activity of endothal as a contact herbicide and defoliant is related to the known irritating toxicity of its parent compound, norcantharidin. However, more recent studies suggest that the herbicidal activity of endothal may be a function primarily of its anti-plant protein phosphatase (PP2A) activity. Li et al., (1993) showed that cantharidin and endothal inhibit spinach leaf PP2A and PP1 and inhibit the activation of nitrate reductase by light in the intact spinach leaf, a process mediated by PP2A. Smith at al. (1994) demonstrate that the structurally unrelated protein phosphatase inhibitors okadaic acid and calyculin-A are potent inhibitors at nanomolar concentrations of the growth of certain plants. The activity of okadaic acid and calyculin-A strongly suggest that the activity of endothal as an herbicide is due to its anti-phosphatase activity.

Baskin and Wilson (1997) showed inhibitors of serine-threonine protein phosphatases including cantharidin inhibit organization of plant microtubules. Ayaydin et al. (2000) show that endothal inhibited PP2A activity causing alteration of cell division in cultured alfalfa cells. They noted that endothal was cell permeable.

The compounds herein, therefore, are useful, commercially feasible, and safer herbicides both with respect human exposure and to the environment.

The compounds disclosed herein are also useful for the treatment of tumors. In one embodiment, the compounds are useful for the treatment of tumors which overexpress N-CoR, TCTP, or both.

The compounds disclosed herein are also useful for the treatment of fungal infections. In one embodiment, the compounds are useful for the treatment of a fungal infections of *T. rubrum*.

The compounds disclosed herein can be obtained by methods described herein and as described in OCT International Application PCT/US08/01549.

The human medulloblastoma cell line DAOY is available from the American Type Culture Collection (ATCC), P.O. Box 1549, Manassa, Va., 20108, as ATCC No. HTB-186.

EXPERIMENTAL DETAILS

Methods and Materials 4.3-[4-(2-Hydroxyethyl)-piperazine-1-carbonyl]-7-oxa-bicyclo[2.2.1]heptane-2-carboxylic acid benzyl ester (12, Compound 109)

Step 1: Synthesis of 7-oxa-bicyclo[2.2.1]heptane-2,3-dicarboxylic acid monobenzyl ester (10)

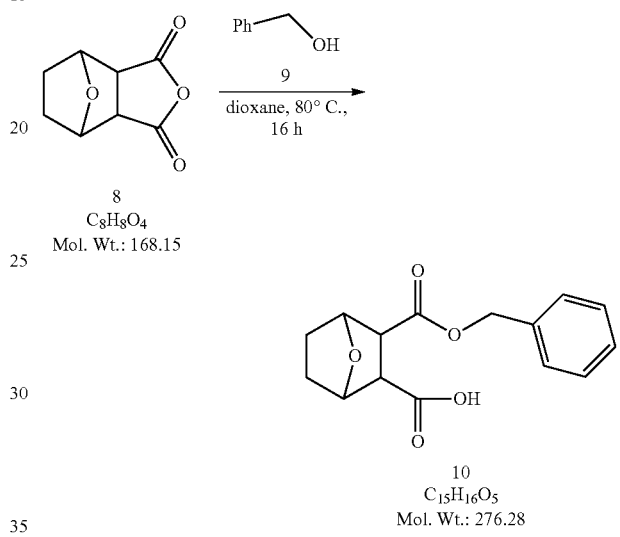

A mixture of 4,10-dioxa-tricyclo[5.2.1.0²,⁶]decane-3,5-dione (8, 3.7 g, 22.0 mmol) and benzyl alcohol (9) (4.5 mL, 44.0 mmol) in dioxane was heated at 80° C. for 16 h. Cooled to room temperature and evaporated to remove solvent. Residue obtained was triturated with diisopropyl ether (20 mL) to give white solid of 10 which was filtered, washed with diisopropyl ether (10 mL) and dried. Yield: 3.6 g (59%). $^1$H NMR (300 MHz, CDCl$_3$) δ 1.45-1.55 (m, 2H); 1.78-1.81 (m, 2H); 3.05 (s, 2H); 4.91 (d, J=9.4 Hz, 2H); 5.02 (d, J=6.3 Hz, 1H); 5.13 (d, J=6.3 Hz, 1H); 7.28-7.40 (m, 5H).

Step 2: 3-[4-(2-Hydroxyethyl)-piperazine-1-carbonyl]-7-oxa-bicyclo[2.2.1]heptane-2-carboxylic acid benzyl ester (12, Compound 109)

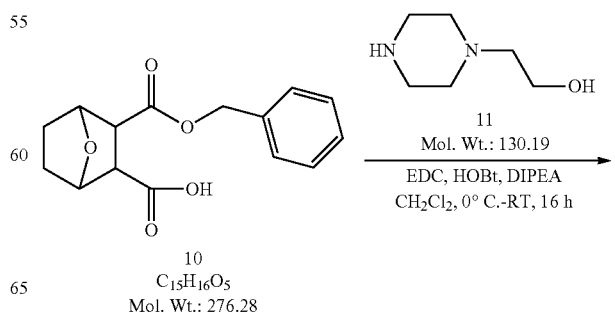

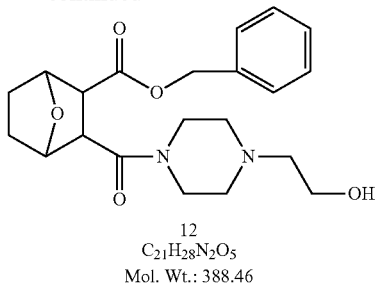

12
C$_{21}$H$_{28}$N$_2$O$_5$
Mol. Wt.: 388.46

To a solution of compound 10 (3.00 g, 11.6 mmol) in CH$_2$Cl$_2$ at 0° C. (60 mL) was added piperazine-1-ethanol (11) (1.82 g, 14.0 mmol), EDC (3.12 g, 16.3 mmol), HOBt (0.20 g) and DIPEA (5.8 mL, 34.9 mmol). The mixture was allowed to warm to RT over 16 h. TLC (5% MeOH/CH$_2$Cl$_2$) showed no starting material. The reaction mixture was diluted with CH$_2$Cl$_2$ (50 mL), washed with water (2×40 mL) and dried. Evaporation of organic layer gave a residue. The residue was triturated with diisopropyl ether (20 mL) to get 3-[4-(2-hydroxy-ethyl)-piperazine-1-carbonyl]-7-oxa-bicyclo[2.2.1] heptane-2-carboxylic acid benzyl ester (12) as a white solid. Yield: 3.24 g (72%). Mp 72-75 C. $^1$H NMR (300 MHz, CDCl$_3$) δ 1.42-1.56 (m, 2H); 1.76-1.82 (m, 2H); 2.02 (s, 2H); 2.29-2.51 (m, 4H); 2.90 (d, J=6.4 Hz, 1H); 3.08 (d, J=6.1 Hz, 1H); 3.18-3.24 (m, 2H); 3.41 (bs, 1H); 3.60 (t, J=2.3 Hz, 2H); 3.69 (bs, 1H); 4.90 (dd, J=6.8 Hz, 2.3 Hz, 2H); 5.08 (s, 2H); 7.28-7.40 (m, 5H).

1,3-(4-Methylpiperazinc-1-carbonyl)-7-oxa-bicyclo[2,2,1]heptane-2-carboxylic acid 4-(2-/<<rf-butoxycarbonylamino-2-carboxyethyl)-phenyl ester (4, Compound 112)

Step 1: 3-(4-Methylpiperazine-1-carbonyl)-7-oxa-bicyclo[2,2,1]heptane-2-carbonyl chloride (1)

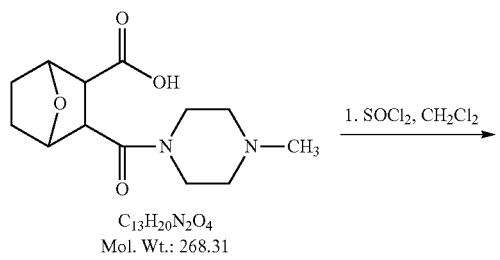

C$_{13}$H$_{20}$N$_2$O$_4$
Mol. Wt.: 268.31

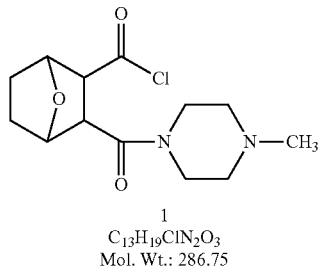

1
C$_{13}$H$_{19}$ClN$_2$O$_3$
Mol. Wt.: 286.75

To an ice-cold solution of 3-(4-methylpiperazine-1-carbonyl)-7-oxa-bicyclo[2,2,1]-heptane-2-carboxylic acid (938 mg, 3.5 mmole) in methylene chloride (30 mL) was added thionyl chloride (1 mL) followed by a few drops of DMF. After stirring at ice-cold temperature for 30 min, the ice-bath was removed and stirring continued at room temperature overnight. The excess thionyl chloride was removed using oil-free vacuum pump at −50° C. and to the residue was added methylene chloride (10 mL). The resulted thin slurry of 1 was used as such in the next reaction.

Step 2: 3-(4-Methylpiperazine-1-carbonyl)-7-oxa-bicyclo[2,2,1]heptane-2-carboxylic acid 4-(2-benzyloxycarbonyl-2-tert-butoxycarbonylamino-2-carboxyethyl)-phenyl ester (3)

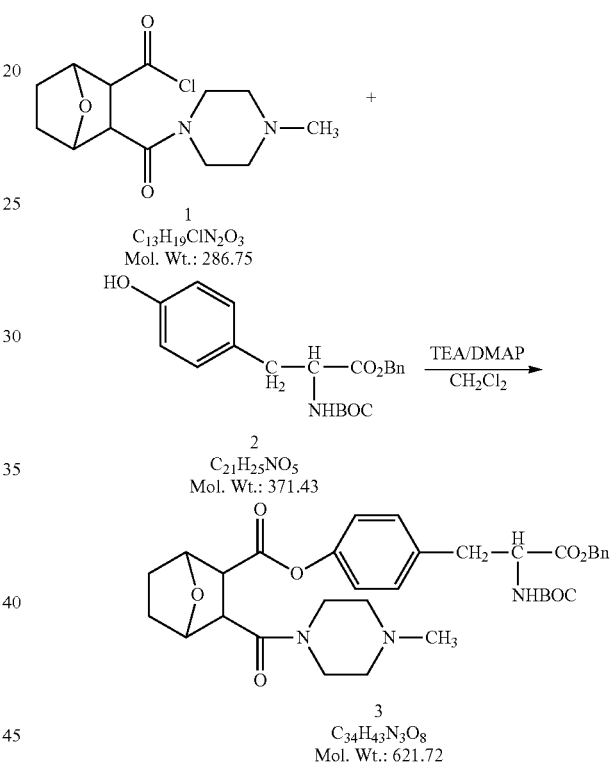

To an ice-cold solution of Boc-L-tyrosine benzyl ester (2, 780 mg, 2.1 mmole) and DMAP (100 mg) in methylene chloride (10 mL) and TEA (2.9 mole, 21 mmole) was added the above suspension of acid chloride (1, 1.0 g, 3.5 mmole) in methylene chloride (10 mL). After stirring for 10 minutes at ice bath temperature, ice-bath was removed and stirred at room temperature for 1 h. At this point the TLC (95:5:: CH$_2$Cl$_2$:MeOH) showed the disappearance of starting material 2. The reaction mixture was diluted with methylene chloride (30 mL) and washed with water (30 mL) followed by brine, dried over anhydrous sodium sulfate, filtered and concentrated. The crude residue was purified by column chromatography using 5% methanol in methylene chloride to give pure required compound 3 (1.040 g, 76%). $^1$H NMR (CDCl$_3$) δ 1.48 (s, 9H), 1.64 (d, 2H), 1.96 (m, 2H), 2.34 (s, 3H), 2.54 (m, 4H), 3.14 (m, 2H), 3.15 (d, J=9.00 Hz, 1H), 3.35 (d, J=9.00 Hz, 1H), 3.67 (m, 4H), 4.62 (m, 1H), 4.91 (d, 1H), 5.0 (m, 1H), 5.20 (m, 3H), 7.06 (m, 4H), 7.40 (m, 5H). EIMS: 621 (M$^+$).

Step 3: 3-(4-Methylpiperazine-1-carbonyl)-7-oxa-bicyclo[2,2,1]heptane-2-carboxylic acid 4-(2-tert-butoxycarbonylamino-2-carboxyethyl)-phenyl ester (4, Compound 112)

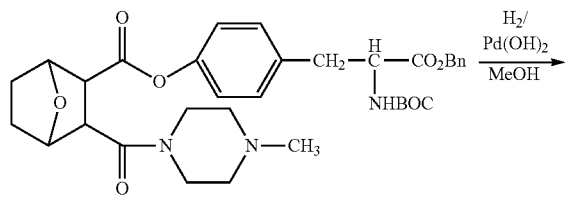

3
$C_{34}H_{43}N_3O_8$
Mol. Wt.: 621.72

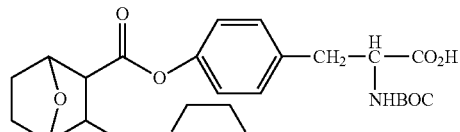

4
$C_{27}H_{37}N_3O_8$
Mol. Wt.: 531.60

A solution of above coupled product 3 (600 mg, 0.965 mmole) in methanol (40 ml) was hydrogenated using hydrogen balloon and Pd(OH)$_2$ (100 mg, 20% Pd on C) as a catalyst overnight. The catalyst was filtered through celite, the filtrate was concentrated to dryness and the residue was triturated with ethyl acetate (15 mL). Separated solid was filtered to give pure title compound 4 as a white solid (460 mg, 89%). Mp 165° C. (decomp). $^1$H NMR (CDCl$_3$) δ 1.44 (s, 9H), 1.60 (m, 2H), 1.81 (m, 2H), 2.48 (s, 3H), 2.93 (m, 5H), 3.01 (m, 1H), 3.22 (m, 1H), 3.32 (m, 1H), 3.35 (m, 1H), 3.68 (m, 4H), 4.41 (m, 1H), 4.79 (d, 1H), 5.07 (d, 1H), 5.32 (m, 1H), 6.95 (d, J=7.00 Hz, 2H), 7.16 (d, J=7.00 Hz, 2H). EST: 530 (M$^+$-H).

2.3-(4-Methylpiperazine-1-carbonyl)-7-oxa-bicyclo[2,2,1]heptane-2-carboxylic acid 4-(2-amino-2-carboxyethyl)-phenyl ester hydrochloride salt (5, Compound 110)

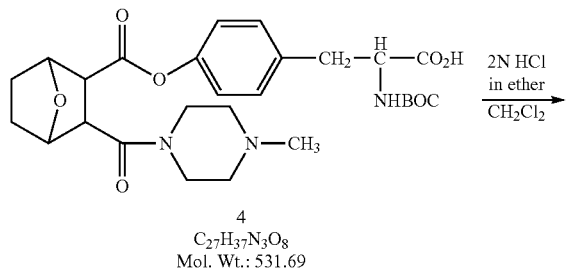

4
$C_{27}H_{37}N_3O_8$
Mol. Wt.: 531.69

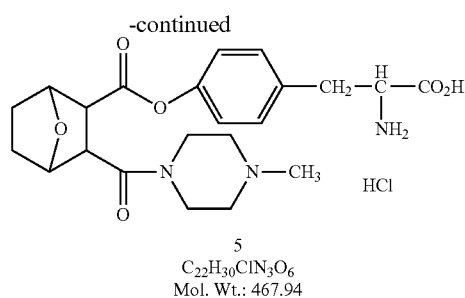

5
$C_{22}H_{30}ClN_3O_6$
Mol. Wt.: 467.94

To an ice-cold solution of BCC derivative (4, 150 mg, 0.28 mmole) in methylene chloride (10 mL) was added a solution of 2M HCl in ether (1 mL). As the addition started to the reaction mixture, the solid started separating out. The suspension was stirred over-night at room temperature. The reaction mixture was concentrated to dryness and co-evaporated with hexane. It was triturated with hexane to give solid which on filtration gave pure title compound 5 as an off white solid (5, 130 mg, 99%). Mp 110° C. (decomp). $^1$HNMR (NaOD/D$_2$O) δ 1.37 (m, 2H), 1.49 (m, 2H), 2.03 (s, 3H), 2.21 (m, 3H), 2.54 (m, 6H), 3.01 (m, 1H), 3.21 (m, 1H), 3.38 (m, 1H), 4.53 (m, 2H), 4.75 (m, 2H), 6.38 (d, 2H), 6.79 (d, 2H). ESMS: 432 (M+H).

3.3-(4-Methyl-piperazine-1-carbonyl)-7-oxa-bicylco[2,2,1]heptane-2-carboxylic acid 2,2,2-trichloroethyl ester (7, Compound 113)

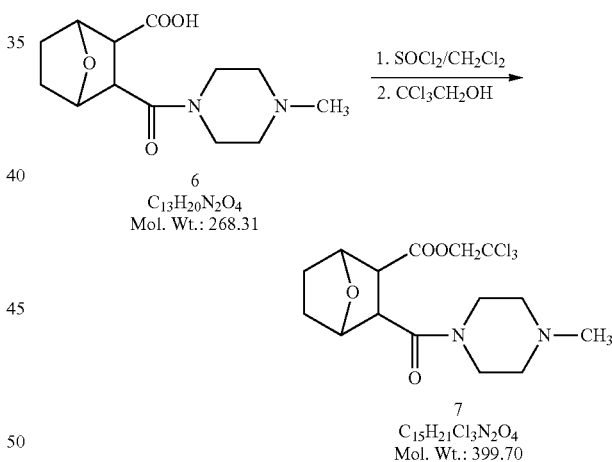

To a suspension of acid (6, 536 mg, 2 mmole) in methylene chloride (15 mL) was added SOCl$_2$ (1 mL) followed by 2 drops of DMF. The reaction mixture was stirred at room temperature overnight. It was still a suspension. To this suspension added trichloroethanol (6 mL). After the addition of trichloroethanol, the reaction mixture became homogeneous. Stirring was continued for 1.5 h followed by evaporation of the solvent. Added ethyl acetate (30 mL) to the residue and extracted with water (2× 25 mL). Water layer neutralized with NaHCO$_3$ to pH 5-6 and evaporated to dryness. The residue dissolved in acetonitrile (30 mL) on heating and the separated NaCl was removed by filtration. The filtrate was treated with charcoal, evaporated to dryness, triturated with hot ethyl acetate and filtered the solid to give pure title ester 7 as colorless crystals. (416 mg, 52%). MP 229-232° C. $^1$H NMR (D40) δ 1.68 (m, 4H), 2.88 (s, 3H), 3.10 (m, 3.48 (m, 5H), 4.25 (m, 2H), 4.76 (m, 5H). EIMS: 399 (M+).

Preparation of 3-[2-(2,5-Dioxo-4,4-diphenyl-imidazolidin-1-yl)-ethylcarbamoyl]-7-oxa-bicyclo(2.2.1]heptane-2-carboxylic acid (3, Compound 114)

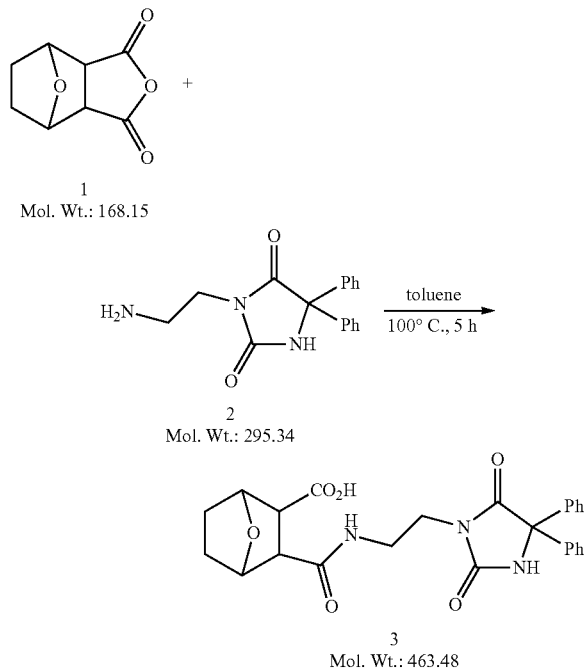

To a mixture of exo-7-oxabicyclo[2.2.1]heptane-2,3-dicarboxylic acid anhydride (504 mg, 3 mmol) and N³-(2-aminoethyl)-5,5-diphenylhydantoin (2.0 g, 6.8 mmol) (prepared according to the procedure reported by Shaffer et. al. *J. Med. Chem.* 1967, W, 739) was added dry toluene (10 mL) and the mixture was heated at 100° C. for 5 h. The solvent was evaporated on rotary evaporator and added water (10 mL) and ethyl acetate (20 mL) to the residue. The solution was made acidic to pH 2 with aq. citric acid (10%) and the organic layer was separated. Aqueous layer was extracted again with EtOAc (2×30 mL). Combined organic layers was washed with water (10 mL), dried ($Na_2SO_4$) and evaporated. The residue was recrystallized from EtOAc to give colorless crystalline desired product. Yield: 700 mg (50%). M.p.: 208-210° C.; $^1$NMR (CDCl$_3$, 300 MHz): δ 1.43-1.48 (m, 2H), 1.66-1.77 (m, 2H), 2.48 (s, 2H), 3.72-3.82 (m, 4H), 4.69-4.71 (m, 2H); 6.47 (bs, 1H), 7.34-7.39 (m, 1 OH); ESI-MS: (m/z) 445 (M+-18).

Example 1

Effect of Compound 110 and Related Analogues on Medulloblastoma DAOY Cells

In Vivo Experiments

Human Medulloblastoma DAOY cells were implanted subcutaneously in the flanks of SCID mice. After 7 days when the implanted tumor cells reached a mass with the average diameter of 6 mm, 6 animals received 0.12 mg of Compound 110, 6 animals received 0.18 mg of Compound 110, and 6 animals received vehicle (PBS) only. After two weeks of treatment, all animals were sacrificed, the subcutaneous tumor masses resected, and their volumes calculated. As shown in FIG. 1, both doses of Compound 110 led to significant inhibition of tumor growth.

Example 2

Inhibition of Growth of Glioblastoma Multiforme Cells of Line 0373 by Exposure for 7 Days to Increasing Concentrations of Compound 109, 110, 112, and 113

Figure 2:
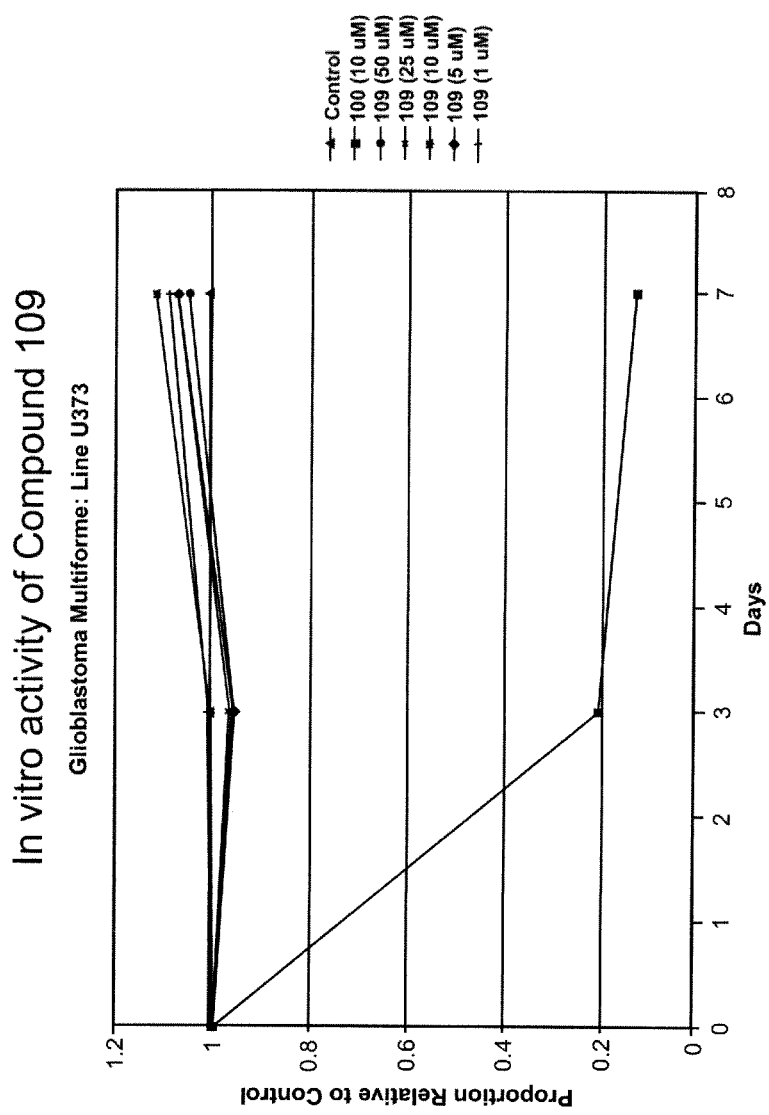
FIG. 2. In vitro activity of Compound 109
Inhibition of growth of glioblastoma multiforme cells of line U373 by exposure for 7 days to increasing concentrations of compound 109 compared to 10 uM compound 100.
Figure 3:
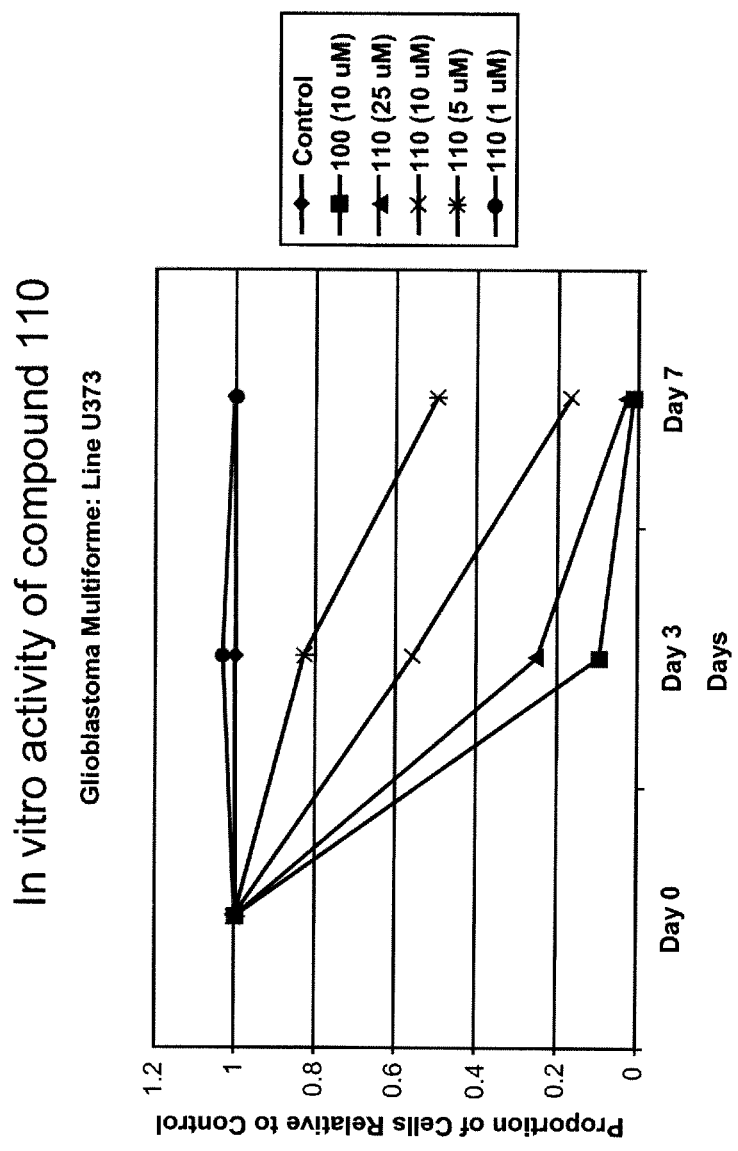
FIG. 3. In vitro activity of compound 110
Inhibition of growth of glioblastoma multiforme cells of line U373 by exposure for 7 days to increasing concentrations of compound 110 compared to 10 uM compound 100.
Figure 4:
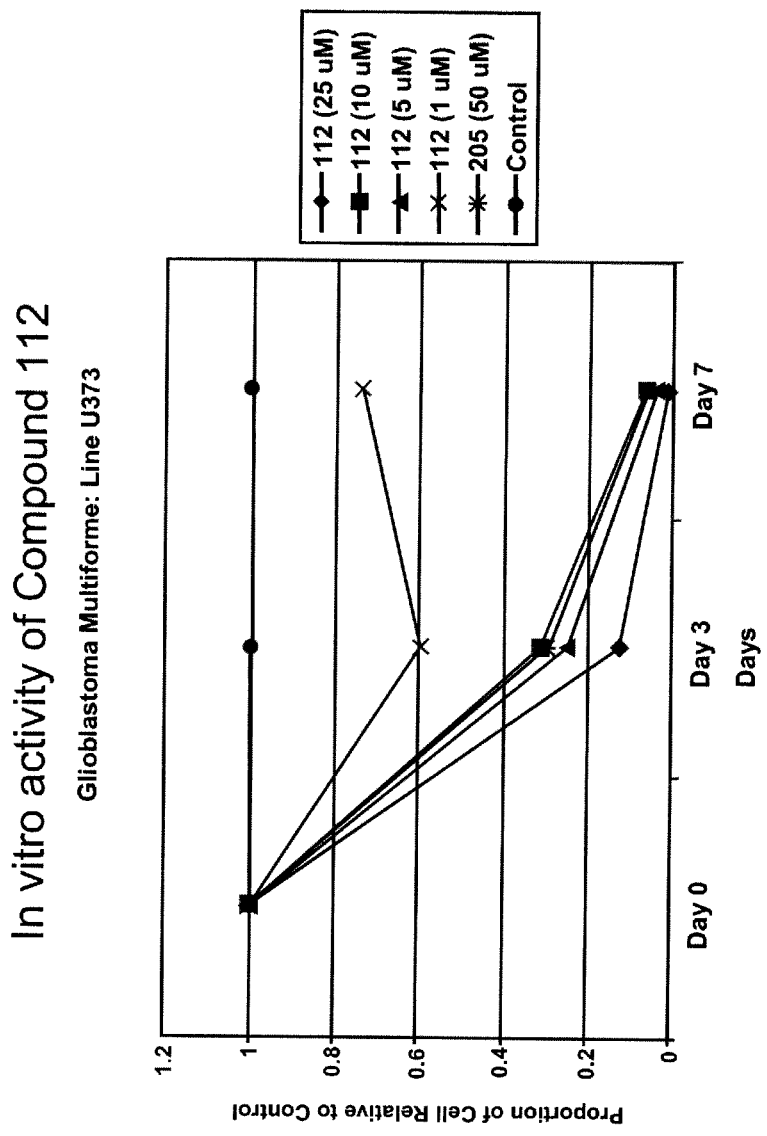
FIG. 4. In vitro activity of compound 112
Inhibition of growth of glioblastoma multiforme cells of line 0373 by exposure for 7 days to increasing concentrations of compound 112 compared to compound 205, a compound known to inhibit this cell line.
Figure 5:
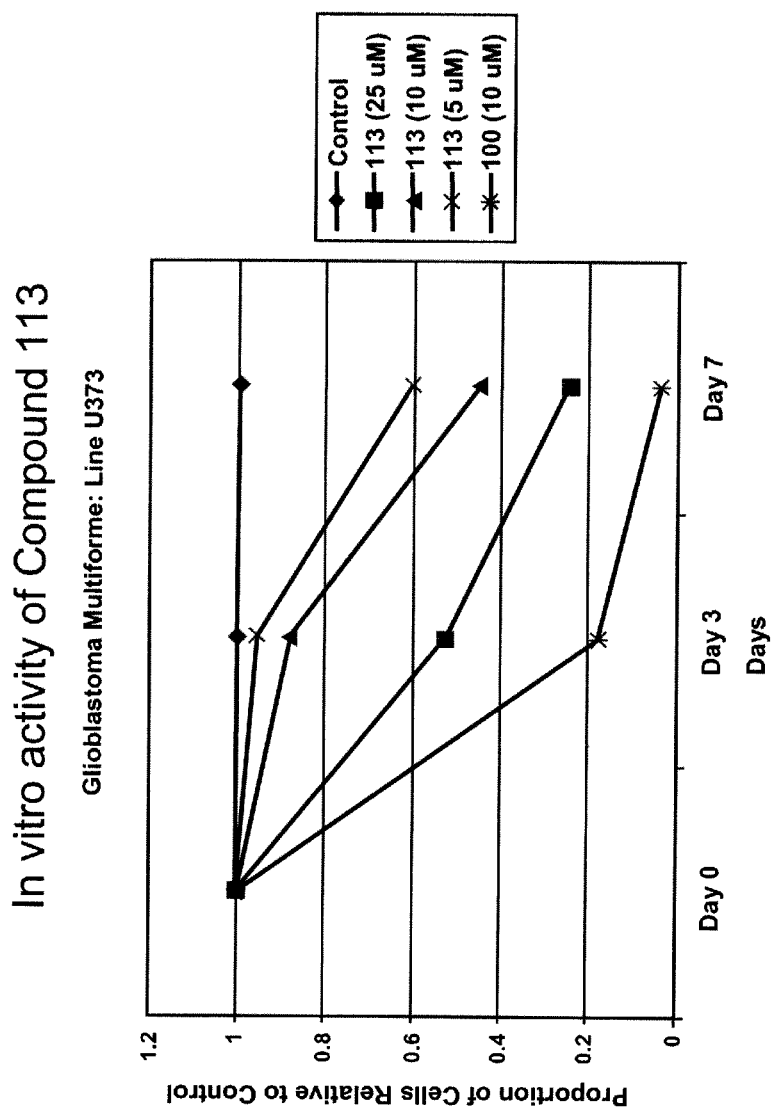
FIG. 5. In vitro activity of compound 113
Inhibition of growth of glioblastoma multiforme cells of line 0373 by exposure for 7 days to increasing concentrations of compound 113 compared to 10 uM compound 100.

At the highest concentrations of compound 109, there is slight inhibition of cell growth after 3 day. At lower concentrations, compound 109 has slight stimulatory activity, increasing over 7 days (FIG. 1). Other compounds of the compound 100 series at very low concentrations have mild to modest stimulator activity on cells in culture that is lost at higher concentrations when the drugs are inhibitory in a dose dependent manner (see FIGS. 2-4). Compounds 110, 112, and 113 inhibited cell growth in a dose dependent manner.

Discussion:

The compounds described herein increase the phosphorylation of several regulatory proteins including Akt. At low doses that are non-toxic to mice, these compounds slightly stimulate cell proliferation and increase phosphorylation of Akt in human cancer cells lines tested, including SH-SY5Y. When given intraperitoneally to normal mice, compounds 110, 113 and 114 also increased Akt phosphorylation in the cell lines tested, as set forth in the examples herein.

Because the compounds increase cellular Akt at low non-toxic doses and also increase acetylation of histones in neurons of the intact animal, these compounds are useful for the treatment of neurodegenerative diseases, particularly Alzheimer's disease and other tauopathies. While each of the compounds increase Akt phosphorylation of multiple tumor cell lines, they also increase Akt phosphorylation of the neuroblastoma cell line SH-SY5Y.

The results with compounds 110, 113 and 114 show that each of these has properties that enhance their entry into the brain.

The mechanism by which the compounds described herein exert their neuroprotective effect may be by increasing the intra-neuronal cell activity of Akt-1 and enhancing the acetylation of neuronal histones. Each of these compounds when given by intraperitoneal injection increase Akt phosphorylation in mouse neurons. This increase in Aky phosphorylation is associated with an increase in the phosphorylation of GSK-3β. Because increased phosphorylation of GSK-3β is known to decrease its activity, chronic suppression of GSK 3β by the compounds described herein may reduce tau phosphorylation. Reduction in tau phosphorylation reduces the formation of paired helical filaments, an intervention that should lessen the progression of tauopathies, including Alzheimer's disease, Parkinson's disease, amyotrophic lateral sclerosis, and other rarer neurodegenerative diseases characterized by abnormal depositions of tau molecules.

REFERENCES

Ayaydin, F. at al., (2000) *The Plant Journal*, 23:85-96.
Baskin, T. and Wilson, J., (1997) *Plant Physiol*. 113:493-502.
Bastien et al., (2004), *Gene*, Vol. 328, pp. 1-16.
Crafts, A. S., (1953) *Rev. Plant. Physiol.*, 4:253-282.
Erdodi, F. et al., (1985) *Am. J. Physiol.*, 269 (*Cell Physiol.* 38) C1176-C1184.
Essers, M. at al., (2001) *Tetrahedron Lett.*, 42, 5429-5433.

Graziano, M. J. and Casida, J. E. (1987) *Toxicol Lett.*, 37, 143-148.

Hart, M E at al. (2004) *Bioorganic & Medicinal Chemistry Letters*, Vol. 14, pp. 1969-1973.

Hermanson at al. (2002) *Nature*, Vol. 419, pp. 934-939.

Honkanan, R. E. et al., (1993) *FEBS Lett.*, 330, 283-286.

Kawamura, N. at al. (1990) *Chem. Res. Toxicol.*, Vol. 3, pp. 318-324.

Li, Y. M. et al., (1992) *Proc. Natl. Acad. Sci. USA*, 89, 11867-11870.

Li, Y. M. at al., (1993) *Biochem. Pharmacol.*, 46, 1435-1443.

Matsuzawa, M. et al. (1987) *J. Agric. Food Chem.*, Col. 35, No. 5.

Sakoff, J A. (2004) *Current Pharmaceutical Design*, Vol. 10, pp. 1139-1159.

Schweizer, H. R., (1989) *Helv. Chim. Acta.*, 2221-2235.

Shimi, I R et al. (1982) *European Journal of Cancer and Clinical Oncology*, 18:785-793.

Singh et al. (2003) *Cancer Research*, Vol. 63, pp. 5821-5828.

Singh et al. (2004 *Nature*, Vol. 432, pp. 396-401.

Smith et al., (1994) *Planta* 194:516-524.

Stupp et al. (2005) *N. Engl. J. Med.*, Vol. 352, pp. 987-996.

Trost, L., (1977) *J. Am. Chem. Soc.*, 99, 7079.

Tsauer, W. et al., (1997) *Anticancer Research* 17, 2095-2098.

Uchida et al. (2000) *Proc. Natl. Acad. Sci. USA*, Vol. 97, pp. 14720-14725.

Wang, D S, (1989) *Journal of Ethnopharmacology*, 26:147-162.

Yi, S N et al., *Bulletin of Hunan Medical University*, (1988), 13:327-330.

U.S. Pat. No. 6,949,624, Liu et al.

U.S. Patent Publication No. 2004/0197888, Armour at al.

U.S. Patent Publication No. 2004/0253637, Buechler et al.

U.S. Patent Publication No. 2005/0203082, Hsu et al.

U.S. Patent Application No. 2006/0030616A1, filed Feb. 9, 2006 (McCluskey at al.)

Wang, G S (1989) *J. Ethnopharmacol.*, Vol. 26, pp. 147-162.

Wang, G S et al. (1986) *Chinese. Pharm. Bull.*, Vol. 21, pp. 90-93.

Wang, G S et al. (1987) *Chinese Pharm. Bull.*, Vol. 22, pp. 517-519.

Yung et al. (1996) *Clin. Cancer Res.* Vol. 2, pp. 1931-1935.

What is claimed is:

1. A compound having the structure

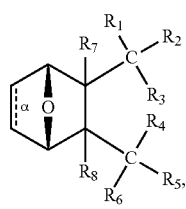

wherein bond α is present or absent;

$R_1$ and $R_2$ is each independently H, O⁻O or $OR_9$, where $R_9$, is H, alkyl, alkenyl, alkynyl or aryl, or $R_1$ and $R_2$, together are =O;

$R_3$ is OH $R_4$ is

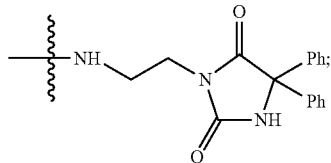 [SMILES: *NCCN1C(=O)NC(c2ccccc2)(c2ccccc2)C1=O]

$R_5$ and $R_6$ is each independently H, OH, or $R_5$ and $R_6$ taken together are =O; and $R_7$ and $R_8$ is each independently H, F, Cl, Br, $SO_2Ph$, $CO_2CH_3$, or $SR_{13}$, where $R_{13}$ is H, aryl or a alkyl, alkenyl or alkynyl, or a salt or enantiomer of the compound.

2. The compound of claim 1, wherein the compound has the structure

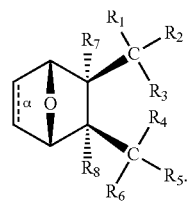

3. The compound of claim 1, wherein bond α is present.

4. The compound of claim 1, wherein bond α is absent.

5. The compound of claim 1, having the structure

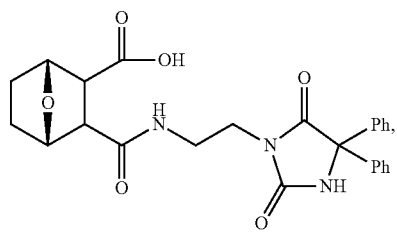 [SMILES: O=C(NCCN1C(=O)NC(c2ccccc2)(c2ccccc2)C1=O)C1C(C(=O)O)[C@H]2CC[C@@H]1O2]

or a salt of the compound.

6. The compound of claim 1, having the structure

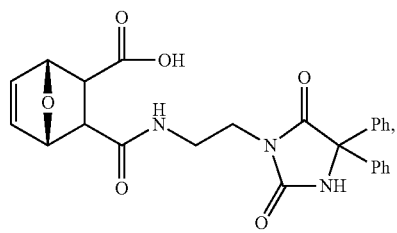 [SMILES: O=C(NCCN1C(=O)NC(c2ccccc2)(c2ccccc2)C1=O)C1C(C(=O)O)[C@H]2C=C[C@@H]1O2]

or a salt of the compound.

7. A pharmaceutical composition comprising the compound of claim 1 and a pharmaceutically acceptable carrier.

8. A process for preparing the compound of claim 5 comprising (a) reacting a compound of the structure

with a compound having the structure

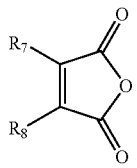

to form an anhydride having the structure

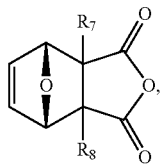

(b) reacting the anhydride having the above structure with a nucleophile having the structure

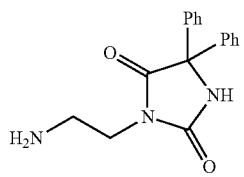 [SMILES: NCCN1C(=O)NC(c2ccccc2)(c2ccccc2)C1=O]

to form compound having the structure

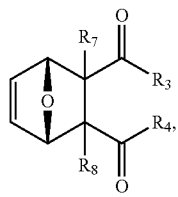

wherein

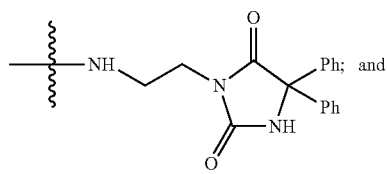 [SMILES: *NCCN1C(=O)NC(c2ccccc2)(c2ccccc2)C1=O]

$R_3$ is OH and $R_4$ is
$R_7$ and $R_8$ are each H,
(c) reacting the product of step (b) with hydrogen in the presence of a catalyst to form a compound having the structure

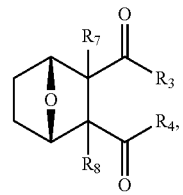

wherein

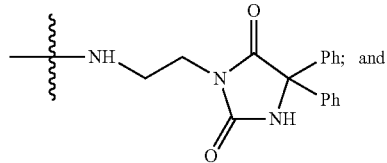 [SMILES: *NCCN1C(=O)NC(c2ccccc2)(c2ccccc2)C1=O]

$R_3$ is OH and $R_4$ is
$R_7$ and $R_8$ are each H.

9. A process for preparing the compound of claim 6 comprising (a) reacting a compound of the structure

with a compound having the structure

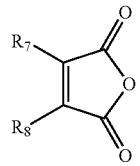

to form an anhydride having the structure

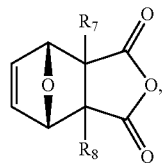

(b) reacting the anhydride having the above structure with a nucleophile having the structure

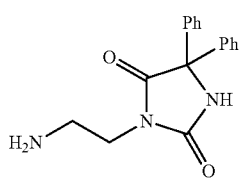 [SMILES: NCCN1C(=O)NC(c2ccccc2)(c2ccccc2)C1=O]

to form compound having the structure
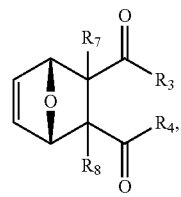
wherein
R₃ is OH and R₄ is
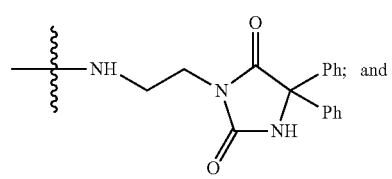 [SMILES: *NCCN1C(=O)NC(c2ccccc2)(c2ccccc2)C1=O]
R₇ and R₈ are each H.
* * * * *